United States Patent
Preuss et al.

(10) Patent No.: US 8,679,765 B2
(45) Date of Patent: Mar. 25, 2014

(54) METHODS AND COMPOSITIONS FOR DIAGNOSIS AND TREATMENT OF MALIGNANT AND NON-MALIGNANT GAMMOPATHIES

(75) Inventors: Klaus-Dieter Preuss, Homburg/Saar (DE); Michael Pfreundschuh, Homburg/Saar (DE)

(73) Assignee: Ludwig Institute for Cancer Research Ltd., New York, NY (US)

( * ) Notice: Subject to any disclaimer, the term of this patent is extended or adjusted under 35 U.S.C. 154(b) by 30 days.

(21) Appl. No.: 13/145,597

(22) PCT Filed: Jan. 22, 2010

(86) PCT No.: PCT/US2010/000160
§ 371 (c)(1),
(2), (4) Date: Sep. 23, 2011

(87) PCT Pub. No.: WO2010/085345
PCT Pub. Date: Jul. 29, 2010

(65) Prior Publication Data
US 2012/0014940 A1 Jan. 19, 2012

Related U.S. Application Data

(60) Provisional application No. 61/146,456, filed on Jan. 22, 2009, provisional application No. 61/221,401, filed on Jun. 29, 2009.

(51) Int. Cl.
*G01N 33/53* (2006.01)
(52) U.S. Cl.
USPC .......................................... 435/7.1; 436/518
(58) Field of Classification Search
None
See application file for complete search history.

(56) References Cited

U.S. PATENT DOCUMENTS

| 2002/0169308 A1 | 11/2002 | Hillman et al. | |
|---|---|---|---|
| 2004/0265849 A1* | 12/2004 | Cargill et al. | 435/6 |
| 2010/0137149 A1* | 6/2010 | Shin et al. | 506/8 |
| 2010/0160177 A1* | 6/2010 | Merbl et al. | 506/9 |

FOREIGN PATENT DOCUMENTS

WO  WO 2004/100774 A2  11/2004

OTHER PUBLICATIONS

Wille et al. (Acta Med Scand 1980 vol. 208, p. 177-182).*
Sompuram et al. (Blood 2008 vol. 111, p. 302-308).*
[No author listed] Suspected Myeloma: Investigation of paraproteinaemia. Hunter New England NSW Health. 6 pages. http://www.haps.nsw.gov.au/Research/Suspected_Myeloma.aspx. Accessed Sep. 19, 2008.
Grass et al., Association of a dominantly inherited hyperphosphorylated paraprotein target with sporadic and familial multiple myeloma and monoclonal gammopathy of undetermined significance: a case-control study. Lancet Oncol. Oct. 2009;10(10):950-6. Epub Sep. 18, 2009.
Grass et al., Risk of Japanese carriers of hyperphosphorylated paratarg-7, the first autosomal-dominantly inherited risk factor for hematological neoplasms, to develop monoclonal gammopathy of undetermined significance and multiple myeloma. Cancer Sci. Mar. 2011;102(3):565-8.
John et al., Mass spectrometrical verification of stomatin-like protein 2 (SLP-2) primary structure. Proteins. Aug. 1, 2006;64(2):543-51.
Kampe et al., Expression of shared idiotypes by paraproteins from patients with monoclonal gammopathy of undetermined significance. Br J Haematol. Aug. 1994;87(4):719-24.
Kirchhof et al., Modulation of T cell activation by stomatin-like protein 2. J Immunol. Aug. 1, 2008;181(3):1927-36.
Owczarek et al., A novel member of the STOMATIN/EPB72/mec-2 family, stomatin-like 2 (STOML2), is ubiquitously expressed and localizes to HSA chromosome 9p13.1. Cytogenet Cell Genet. 2001;92(3-4):196-203.
Owen et al., Clinicopathological correlates of IgM paraproteinemias. Clin Lymphoma. Jun. 2000;1(1):39-43; discussion 44-5.
Preuss et al., A frequent target of paraproteins in the sera of patients with multiple myeloma and MGUS. Int J Cancer. Aug 1, 2009;125(3):656-61.
Wang et al., Identification and characterization of human SLP-2, a novel homologue of stomatin (band 7.2b) present in erythrocytes and other tissues. J Biol Chem. Mar. 17, 2000;275(11):8062-71.
Zhang et al., Stomatin-like protein 2 is overexpressed in cancer and involved in regulating cell growth and cell adhesion in human esophageal squamous cell carcinoma. Clin Cancer Res. Mar. 1, 2006;12(5):1639-46.

* cited by examiner

*Primary Examiner* — Jacob Cheu
(74) *Attorney, Agent, or Firm* — Wolf, Greenfield & Sacks, P.C.

(57) ABSTRACT

The invention relates, at least in part, to the identification of paratarg as a paraprotein target in various malignant and non-malignant gammopathies, which can be used in the diagnosis and treatment of either.

16 Claims, 16 Drawing Sheets

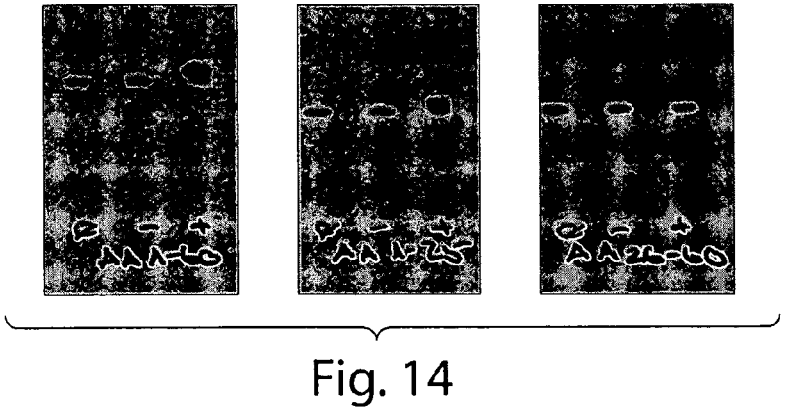
Fig. 14
MUTAGENISATION OF PARATARG FRAGMENT aa 1-60
- ...11-ALLLR.GSLLA.SGRAP.RRASS.GL PRN.TVVLF-40...
- ...11-ALLLR.GALLA.SGRAP.RRASS.GL PRN.TVVLF-40...
- ...11-ALLLR.GSLLA.AGRAP.RRASS.GL PRN.TVVLF-40...
- ...11-ALLLR.GALLA.AGRAP.RRASS.GL PRN.TVVLF-40...
ONLY THE REGION OF INTEREST IS SHOWN.
Fig. 15A
RECOMBINANT MUTATED FRAGMENTS TESTED FOR HYPERPHOSPHORYLATION
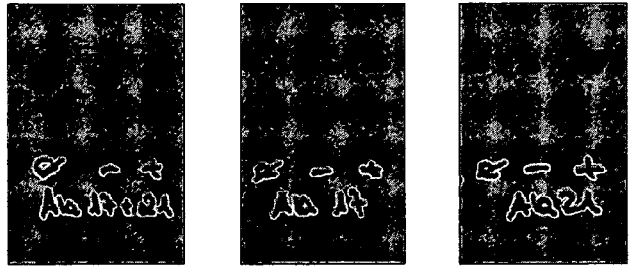
WITHOUT SERINE   Ala17   Ser17
(Ser17Ala+Ser21Ala)   Ser21   Ala21
                   (Ser17->Ala17)  (Ser21->Ala21)
Fig. 15B

**IDENTIFICATION OF KINASE II
PKC ISOFORM I**

| INHIBITOR | CONC. | EXPECTED | |
|---|---|---|---|
| BIM_I | 150 µM | α + β + ε SENSITIVE | HYPERPHOSPHORYLATION IS INSENSITIVE IN ALL CASES ANALYSED |
| | 20 µM | α + β SENSITIVE | => PKCdelta or PKCzeta |
| ROTTLERIN | 50 µM | α + β + γ + δ SENSITIVE | |
| | 5 µM | δ SENSITIVE | |

Fig. 16B

**IDENTIFICATION OF KINASE III
PKC ISOFORM II**

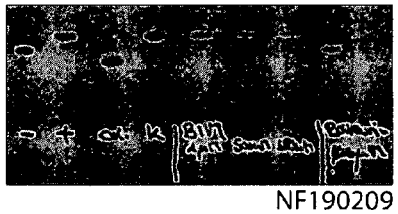

NF190209

| INHIBITOR | CONC. | ESPECTED | |
|---|---|---|---|
| BIM_I | 1 µM | INSENSITIVE | |
| | 500 µM | INSENSITIVE | => PKCzeta |
| | 150 µM | INSENSITIVE | |
| ROTTLERIN | 100 µM | SENSITIVE | |

Fig. 16C

IDENTIFICATION OF THE KINASE IV
PKC ISOFORM, CONFIRMATION
WITH PSEUDOSUBSTRATE

NF050309

K DMSO CONTROL
B BMI (6 µM)
P PSEUDOSUBSTRATE (50 µM)

IDENTIFICATION OF THE KINASE V
DIRECT INTERACTION OF PARATARG WITH PKCzeta
SHOWN BY CO-IMMUNOPRECIPITATION

- UNRELATED ANTIBODY
+ α STOML2

**DIRECT INTERACTION OF 17Ser OF PARATARG
WITH PKCzeta**
CO-IMMUNOPRECIPITATION USING MUTAGENISED FRAGMENTS

BCR CLONING, EXPRESSION, CHARACTERIZATION
(EXAMPLE Pat.#5, VH1-69 J6-01 K3-20, 90% KM-Infilt.)

BCR CLONING, EXPRESSION, CHARACTERIZATION
(EXAMPLE Pat.#5, VH1-69 J6-01 K3-20, 90% KM-Infilt.)

BCR CLONING, EXPRESSION, CHARACTERIZATION
(EXAMPLE Pat.#5, VH1-69 J6-01 K3-20, 90% KM-Infilt.)

BCR CLONING, EXPRESSION, CHARACTERIZATION
(EXAMPLE Pat.#5, VH1-69 J6-01 K3-20, 90% KM-Infilt.)

METHODS AND COMPOSITIONS FOR DIAGNOSIS AND TREATMENT OF MALIGNANT AND NON-MALIGNANT GAMMOPATHIES

RELATED APPLICATIONS

This application is a national stage filing under 35 U.S.C. §371 of international application PCT/US2010/000160, filed Jan. 22, 2010, which was published under PCT Article 21(2) in English, and claims the benefit under 35 U.S.C. §119(e) of U.S. provisional application Ser. No. 61/146,456, filed on Jan. 22, 2009, and U.S. provisional application Ser. No. 61/221,401, filed on Jun. 29, 2009, the entire disclosures of which are incorporated herein by reference.

FIELD OF THE INVENTION

The invention relates, at least in part, to malignant and non-malignant gammopathies.

BACKGROUND OF THE INVENTION

Gammopathy is a collective term referring to various diseases or conditions characterized by an abnormal level of immunoglobulin, termed paraprotein, in affected patients. In monoclonal gammopathies, one specific monoclonal immunoglobulin is produced in excess amounts. Gammopathies can be of malignant or non-malignant nature. Multiple myeloma (MM), sclerotic myeloma, Waldenström macroglobulinemia (WM), immunocytic lymphoma, follicular lymphoma, B cell lymphoma (e.g. immunoblastoma), and chronic B cell lymphocytic leukemia associated with IgM monoclonal proteins, are all examples of malignant gammopathies. Benign gammopathies are collectively referred to as gammopathies of undetermined significance (MGUS).

Multiple myeloma, also known as MM, myeloma, plasma cell myeloma, or as Kahler's disease (after Otto Kahler) accounts for 1% of all malignancies, and for over 10% of the hematological malignancies with a prevalence peak at around 70 years of age. It is the second most common hematologic malignancy in the United States (Katzel et al, 2007) and is regarded as incurable. However, remissions may be induced with steroids, chemotherapy, thalidomide and stem cell transplants. The disease is characterized by neoplastic proliferation of a single plasma cell clone producing a monoclonal immunoglobulin termed paraprotein, M-protein or M-component (Kyle, 1994), which can be detected as a predominant spike in the densitometric analysis of the y globulin fraction area or as a sharp dominant band in immunofixation (Jeppsson et al, 1979). The identification of the antigenic stimuli of such B-cell neoplasms might have considerable impact on our understanding of the pathogenesis of MM, because a causal relationship between these neoplasms and antigenic stimulation has been suggested.

Waldenström macroglobulinemia (WM) is a condition characterized by the presence of a high level of a monoclonal immunoglobulin of the IgM type, elevated serum viscosity, and the presence of a lymphoplasmacytic infiltrate in the bone marrow. WM is a clonal disorder of B lymphocytes and is considered to be a lymphoplasmacytic lymphoma as defined by the World Health Organization (WHO) classification. The clinical manifestations of this condition result from the presence of the paraprotein and malignant lymphoplasmacytic cell infiltration of the bone marrow and other tissue sites. WM is similar to MM, except that organomegaly is common in Waldenström macroglobulinemia and is uncommon in multiple myeloma and lytic bone disease and renal disease are uncommon in Waldenström macroglobulinemia but are common in multiple myeloma.

Malignant gammopathies are often preceded by benign gammopathies. For example, MM is often preceded by monoclonal gammopathy of undetermined significance (MGUS), a benign disorder with a strikingly elevated monoclonal immunoglobulin (or paraprotein-) level of less than 30 g/L in individuals lacking evidence of MM or other lymphoproliferative malignancies. Long-term follow-up of patients with MGUS reveals a 1% to 3% annual risk of developing MM or, to a lesser extent, other lymphoproliferative malignancies. Although investigators have recently described potential models of pathogenesis of gammopathies, such as MGUS and MM, it is unknown whether non-malignant gammopathies precede all malignant gammopathies, for example if all cases of MM are preceded by MGUS, or if malignant gammopathies, for example MM, can arise de novo without preceding MGUS (Landgren et al, 2006).

Paraproteins or monoclonal immunoglobulins characteristic for gammopathies may consist of intact immunoglobulin molecules or of heavy or light chains only. Depending on their rate of production and/or secretion they may accumulate in the serum and/or urine of patients. Their presence in the circulation may remain silent, as in MGUS, or may lead to clinical syndromes such as hyperviscosity, acrocyanosis, cold hemagglutination, hemolysis and hemorrhagic manifestations. Their tissue deposition may be localized, with the kidney being the most frequent target as in myeloma cast nephropathy or systemic, as in AL amyloidosis where heart, liver, nerves, tongue are usual targets, in addition to the kidneys.

So far, two systematic approaches were pursued to characterize the antigenic targets of paraproteins characteristic for gammopathies. One approach was founded on screening cDNA expression libraries of different origins for high affinity binding partners of paraproteins (Preuss et al, 2007). These led to the identification of antigenic targets with affinity greater $1:10^8$ such as autoantigenic targets like TPP2 (titer) $\sim 10^{10}$) or (IGFBP-2) (titer $\sim 10^9$), or food antigens (porcine kinesin, titer $\sim 10^9$). However, all these targets were individually specific and reacted with the paraprotein of only one patient.

Another approach was the usage of phage display random peptide libraries with the goal to identify binding epitopes which should allow the identification of the antigen by searching non-redundant protein databases. This attempt also identifies single protein events like human cytomegalovirus envelop proteins (titer $\sim 2 \times 10^3$) (Sompuram et al, 2008) or only some consensus epitopes with titers $\sim 10^5$, but no corresponding proteins could be identified (Szecsi et al, 1999).

To date, antigenic targets of paraproteins were discovered accidentally due to clinical symptoms caused by the paraprotein (e.g., chronic cold agglutinin disease or cryoglobulinemia (Seligmann & Brouet, 1990) or bleeding disorder (Colwell et al, 1997), because of interference of the paraprotein with laboratory tests ordered for the clinical work-up of the patient (e.g., HIV-1 p24 antigen in an HIV-infected patient with myeloma (Konrad et al, 1993)) or by screening paraproteins against predefined antigens (e.g., anti-streptolysin, anti-DNA, anti-IgG (Seligmann & Brouet, 1990)).

SUMMARY OF THE INVENTION

The lack of knowledge regarding antigenic paraprotein targets in gammopathies not only hampers a deeper understanding of the underlying pathomechanisms, but, more importantly, translates into a lack of a focused approach for diagnosis and therapy of both malignant and non-malignant gammopathies. Accordingly, the identification of a common antigenic paraprotein target in various gammopathies, including MM, MGUS and WM, is a breakthrough discovery with immediate applications in the diagnosis and therapy of these diseases.

We have identified paratarg (stomatin-like protein 2) as an antigenic paraprotein target in a significant portion of MGUS-positive human subjects. Paratarg and paratarg epitopes, antibodies specifically binding paratarg or paraproteins targeting paratarg, compositions containing paratarg and/or the above mentioned antibodies, and methods for using paratarg and the above mentioned antibodies have been identified, providing, for the first time, a focused approach for the diagnosis and treatment of MGUS, MM, WM, and other malignant and non-malignant gammopathies.

Some aspects of this invention relate to methods of determining a level of a paraprotein that selectively binds to paratarg in a body fluid of a subject, and comparing said level of said paraprotein to a reference or control level, wherein if the level of said paraprotein in said body fluid is higher than the reference or control level, then the subject is indicated as having a gammopathy, and wherein if the level of said paraprotein in said body fluid is not substantially different from the reference or control level, then the subject is not indicated as having a gammopathy. In some embodiments, the step of determining the level of the paraprotein includes obtaining a sample of a body fluid from said subject, and mixing said sample with a reagent that selectively binds to said paraprotein, said paraprotein selectively binding paratarg, and/or contacting said sample with a device for assaying the level of one or more of said specific paraprotein/s. In some embodiment, the body fluid is blood, serum, lymph, saliva, urine or cerebrospinal fluid. In some embodiments, the level of said paraprotein that selectively binds paratarg is determined by an immunoassay that includes contacting said body fluid with an antibody that selectively binds said paraprotein, and detecting and/or quantifying the binding of said antibody to said paraprotein. In some embodiments, the immunoassay is a western blotting assay, an enzyme-linked immunosorbent assay (ELISA), an enzyme-linked immunospot assay (ELISPOT), a lateral flow test assay, an enzyme immunoassay (EIA), a fluorescent polarization immunoassay (FPIA), a chemiluminescent immunoassay (CLIA), an antibody sandwich capture assay, or an isoelectric focusing assay. In some embodiments, the level of the paraprotein that selectively binds to paratarg is determined by an immunoassay that includes contacting said body fluid with paratarg, or an epitope thereof, or phosphorylated paratarg, or an epitope thereof, and detecting and/or quantifying the binding of said paratarg, or epitope thereof, or phosphorylated paratarg, or epitope thereof, to said paraprotein. In some embodiments, the paratarg is human paratarg (SEQ ID NO: 1) (RefSeq: NP_038470). In some embodiments, said immunoassay is a western blotting assay, an enzyme-linked immunosorbent assay (ELISA), an enzyme-linked immunospot assay (ELISPOT), a lateral flow test assay, an enzyme immunoassay (EIA), a fluorescent polarization immunoassay (FPIA), a chemiluminescent immunoassay (CLIA), an antibody sandwich capture assay, or an isoelectric focusing assay. In some embodiments, the paratarg or epitope thereof used to contact the paraprotein includes a substitution of one or more amino acid residues amenable to phosphorylation with a different amino acid residue mimicking phosphorylation of said paratarg or epitope thereof. In some embodiments, the paratarg or epitope thereof used to contact the paraprotein includes a substitution of one or more serine residues of amino acids 13-31 of human paratarg (SEQ ID NO: 1). In some embodiments, the paratarg or epitope thereof used to contact the paraprotein includes a substitution of one or more Ser residues of amino acids 17-31 of human paratarg (SEQ ID NO: 1) with a Glu and/or Asp and/or Phe residue. In some embodiments, the paratarg or epitope thereof used to contact the paraprotein comprises a substitution of 17Ser of human paratarg (SEQ ID NO: 1) with a Glu and/or Asp and/or Phe residue. In some embodiments, the paratarg is phosphorylated paratarg. In some embodiments, the phosphorylated paratarg is phosphorylated on one or more Ser residues of amino acids 17-31 of human paratarg (SEQ ID NO: 1). In some embodiments, the phosphorylated paratarg is phosphorylated on 17Ser of human paratarg (SEQ ID NO: 1). In some embodiments, the gammopathy is a malignant gammopathy. In some embodiments, the malignant gammopathy is multiple myeloma. In some embodiments, the malignant gammopathy is sclerotic myeloma. In some embodiments, the malignant gammopathy is Waldenström macroglobulinemia. In some embodiments, the malignant gammopathy is immunocytic lymphoma. In some embodiments, the malignant gammopathy is follicular lymphoma. In some embodiments, the malignant gammopathy is B cell lymphoma. In some embodiments, the gammopathy is a non-malignant gammopathy. In some embodiments, the gammopathy is a monoclonal gammopathy of undetermined significance (MGUS). In some embodiments, the control or reference level is based on the level found in at least one subject not having a gammopathy. In some embodiments, the subject is a blood or organ donor, and the level of paraprotein that selectively binds to paratarg is determined before the blood or organ donated by the subject is administered or transferred to a recipient. In some embodiments, if the subject is indicated as having a gammopathy, then the blood or organ donated by the subject is disqualified for administration or transfer to the recipient, or, if the subject is indicated as not having a gammopathy, then the blood or organ donated by the subject is not disqualified for administration or transfer to the recipient. In some embodiments, the methods according to aspects of this invention further include preparing a report that indicates the status of the subject with respect to gammopathies. In some embodiments, the methods according to aspects of this invention further include providing the analysis of the body fluid, cell, or tissue to a clinician administering health care to the subject. In some embodiments, the methods according to aspects of this invention further include administering health care to the subject based on the status of the subject with respect to gammopathies.

Some aspects of this invention relate to methods that include determining a level of paratarg in a body fluid of a subject, and comparing said level of paratarg to a reference or control level, wherein if the level of paratarg in the sample is higher than the reference or control level, then the subject is indicated as having a gammopathy, and wherein if the level of paratarg is not substantially different from the reference or control level, then the subject is not indicated as having a gammopathy. In some embodiments, the step of determining the level of paratarg includes obtaining a sample of a body fluid from said subject, and mixing said sample with a reagent that selectively binds to paratarg, and/or contacting said sample with a device for assaying the level of paratarg. In some embodiments, the body fluid is blood, serum, lymph, saliva, urine or cerebrospinal fluid. In some embodiments, the level of paratarg is determined by an immunoassay that includes contacting said body fluid with an antibody that selectively binds paratarg, and detecting and/or quantifying the binding of said antibody to paratarg. In some embodiments, said immunoassay is a western blotting assay, an enzyme-linked immunosorbent assay (ELISA), an enzyme-linked immunospot assay (ELISPOT), a lateral flow test assay, an enzyme immunoassay (EIA), a fluorescent polarization immunoassay (FPIA), a chemiluminescent immunoassay (CLIA), an antibody sandwich capture assay, or an isoelectric focusing assay. In some embodiments, the paratarg is phosphorylated paratarg. In some embodiments, the paratarg is phosphorylated on/in one or more of amino acids 17-31 of human paratarg (SEQ ID NO: 1). In some embodiments, the paratarg is phosphorylated on amino acid 17 (Ser) of human paratarg (SEQ ID NO: 1). In some embodiments, the gammopathy is multiple myeloma. In some embodiments, the gammopathy is a malignant gammopathy. In some embodiments, the malignant gammopathy is multiple myeloma. In some embodiments, the malignant gammopathy is sclerotic myeloma. In some embodiments, the malignant gammopathy is Waldenström macroglobulinemia. In some embodiments, the malignant gammopathy is immunocytic lymphoma. In some embodiments, the malignant gammopathy is follicular lymphoma. In some embodiments, the malignant gammopathy is B cell lymphoma. In some embodiments, the gammopathy is a non-malignant gammopathy. In some embodiments, the gammopathy is a monoclonal gammopathy of undetermined significance (MGUS). In some embodiments, the control or reference level is based on the level found in at least one subject not having a gammopathy. In some embodiments, the subject is a blood or organ donor, and the level of paratarg is determined before the blood or organ donated by the subject is administered or transferred to a recipient. In some embodiments, if the subject is indicated as having a gammopathy, then the blood or organ donated by the subject is disqualified for administration or transfer to the recipient, or, if the subject is indicated as not having a gammopathy, then the blood or organ donated by the subject is not disqualified for administration or transfer to the recipient. In some embodiments, the methods according to aspects of this invention further include preparing a report that indicates the status of the subject with respect to gammopathies. In some embodiments, the methods according to aspects of this invention further include providing the analysis of the body fluid, cell, or tissue to a clinician administering health care to the subject. In some embodiments, the methods according to aspects of this invention further include administering health care to the subject based on the status of the subject with respect to gammopathies.

Some aspects of this invention relate to isolated antibodies or antigen-binding fragments thereof that selectively binds a paraprotein that selectively binds paratarg. In some embodiments, the paratarg is phosphorylated paratarg. In some embodiments, said antibody is a monoclonal antibody, human monoclonal antibody, a humanized monoclonal antibody, a chimeric monoclonal antibody, or a single-domain antibody. In some embodiments, said fragment is a Fab fragment, a F(ab)2 fragment, or a F(ab') fragment. In some embodiments, said antibody, or antigen-binding fragment thereof, is conjugated to a therapeutic, cytotoxic or diagnostic agent. In some embodiments, said antibody, or antigen-binding fragment thereof, fused to a therapeutic, cytotoxic or diagnostic agent. In some embodiments, the therapeutic, cytotoxic or diagnostic agent is a cytotoxic radionuclide, a radiotherapeutic isotope, an enidyene, duocarmycin, methothrexate, doxorubicin, melphalan, chlorambucil, ARA-C, vindesine, mitomycin C, cisplatin, etoposide, bleomycin or 5-fluorouracil. In some embodiments, said antibody or antigen binding fragment thereof is attached to a solid support. Some aspects of this invention relate to compositions including an isolated antibody or antigen-binding fragment thereof, that selectively binds a paraprotein that selectively binds paratarg. In some embodiments, the composition includes a pharmaceutically acceptable carrier.

Some aspects of this invention relate to isolated antibodies or antigen-binding fragments thereof that selectively binds phosphorylated paratarg or a phosphorylated epitope thereof. In some embodiments, the paratarg is phosphorylated paratarg. In some embodiments, said antibody is a monoclonal antibody, a human monoclonal antibody, a humanized monoclonal antibody, a chimeric monoclonal antibody, or a single-domain antibody. In some embodiments, said fragment is a Fab fragment, a F(ab)2 fragment, or a F(ab') fragment. In some embodiments, the isolated antibody or antigen-binding fragment thereof is conjugated to a therapeutic, cytotoxic or diagnostic agent. In some embodiments, the isolated antibody or antigen-binding fragment thereof is fused to a therapeutic, cytotoxic or diagnostic agent. In some embodiments, the therapeutic, cytotoxic or diagnostic agent is a cytotoxic radionuclide, a radiotherapeutic isotope, an enidyene, duocarmycin, methothrexate, doxorubicin, melphalan, chlorambucil, ARA-C, vindesine, mitomycin C, cisplatin, etoposide, bleomycin or 5-fluorouracil. In some embodiments, the isolated antibody or antigen-binding fragment thereof is attached to a solid support. Some aspects of this invention relate to compositions including an isolated antibody, or antigen-binding fragment thereof, that selectively binds phosphorylated paratarg or a phosphorylated epitope thereof. In some embodiments, the composition includes a pharmaceutically acceptable carrier.

Some aspects of this invention relate to isolated phosphorylated paratarg, or an epitope thereof. In some embodiments, the phosphorylated paratarg or epitope thereof includes a peptide showing no homology with other peptides or proteins of the stomatin family. In some embodiments, the phosphorylated paratarg or epitope thereof includes amino acids 17-31 of human paratarg (SEQ ID NO: 1). In some embodiments, the phosphorylated paratarg or epitope thereof includes a fragment of amino acids 17-31 of human paratarg (SEQ ID NO: 1). In some embodiments, the phosphorylated paratarg or epitope thereof comprises 17Ser of human paratarg (SEQ ID NO: 1). In some embodiments, the epitope includes at least eight amino acids. In some embodiments, the phosphorylated paratarg or epitope thereof includes amino acids 10-17, 11-18, 12-19, 13-20, 14-21, 15-22, 16-23, 17-24, 18-25, 19-26, 20-27, 21-28, 22-29, 23-30, and/or 24-31. In some embodiments, the phosphorylated paratarg or epitope thereof includes amino acids 17-25 of human paratarg (SEQ ID NO: 1), or a fragment thereof. In some embodiments, the phosphorylated paratarg epitope includes at least eight amino acids. In some embodiments, the phosphorylated paratarg epitope includes amino acids 17-25 of human paratarg (SEQ ID NO: 1). In some embodiments, the phosphorylated paratarg epitope includes a substitution of one or more amino acids that can be phosphorylated with amino acids mimicking said one or more amino acids in their phosphorylated state. In some embodiments, the phosphorylated paratarg or epitope thereof includes a substitution of one or more Ser residues with a Glu and/or Asp and/or Phe residue. In some embodiments, the substitution is at 17Ser. In some embodiments, the phosphorylated paratarg or epitope thereof includes one or more modified peptide bonds. In some embodiments, the modified peptide bonds are non-hydrolyzable. In some embodiments, the phosphorylated paratarg or epitope thereof is conjugated to a therapeutic, cytotoxic or diagnostic agent. In some embodiments, the phosphorylated paratarg or epitope thereof is fused to a therapeutic, cytotoxic or diagnostic agent. In some embodiments, the therapeutic, cytotoxic or diagnostic agent is a cytotoxic radionuclide, a radiotherapeutic isotope, an enidyene, duocarmycin, methothrexate, doxorubicin, melphalan, chlorambucil, ARA-C, vindesine, mitomycin C, cisplatin, etoposide, bleomycin or 5-fluorouracil. In some embodiments, the phosphorylated paratarg or epitope thereof is attached to a solid support.

Some aspects of this invention relate to compositions including phosphorylated paratarg or epitope thereof in any form described above. In some embodiments, the composition includes a pharmaceutically acceptable carrier.

Some aspects of this invention relate to kits for detecting paratarg, or an epitope thereof, or a paraprotein, or fragment thereof, that selectively binds paratarg, including an antibody, or fragment thereof, selectively binding phosphorylated paratarg, and/or an antibody, or fragment thereof, selectively binding a paraprotein selectively binding phosphorylated paratarg, and/or phosphorylated paratarg, or an epitope thereof. All of these reagents can be in any form described herein, for example peptides and/or proteins may include amino acid substitutions or be conjugated to a reagent as described herein, compositions may contain pharmaceutically suitable substances, et cetera.

Some aspects of this invention relate to methods of treating a subject having or suspected of having paratarg positive gammopathy or multiple myeloma, including reducing the level or biological activity of a paraprotein that selectively binds phosphorylated paratarg in said subject. In some embodiments, the method includes administering to said subject a compound or composition, including an agent capable of reducing the level or biological activity of said paraprotein, in an amount sufficient to reduce said level or biological activity. In some embodiments, the method includes administering to said subject an antibody, or fragment thereof, selectively binding phosphorylated paratarg, and/or a composition containing such an antibody, and/or an antibody, or fragment thereof, selectively binding a paraprotein selectively binding phosphorylated paratarg, and/or a composition containing such an antibody, and/or phosphorylated paratarg, or an epitope thereof, and/or a composition containing phosphorylated paratarg or an epitope thereof. All of these reagents can be in any form described herein, for example peptides and/or proteins may include amino acid substitutions or be conjugated to a reagent as described herein, compositions may contain pharmaceutically suitable substances, et cetera. In some embodiments, the method includes obtaining a body fluid from said subject, decreasing the level of a paraprotein that selectively binds paratarg in said body fluid of said subject, and returning said body fluid to said subject. In some embodiments, the method includes contacting said body fluid with paratarg under conditions in which said paratarg will bind to said paraprotein, and physically separating the fraction of paratarg-bound paraprotein from the body fluid.

Some aspects of this invention relate to methods of treating a subject having or suspected of having paratarg positive gammopathy or multiple myeloma, including reducing the level or biological activity of phosphorylated paratarg in said subject. In some embodiments, the method includes administering to said subject a compound or composition, including an agent capable of reducing the level or biological activity of phosphorylated paratarg, in an amount sufficient to reduce said level or biological activity. In some embodiments, the method includes administering to said subject an antibody, or fragment thereof, selectively binding phosphorylated paratarg, and/or a composition containing such an antibody and/or an antibody, or fragment thereof, selectively binding a paraprotein selectively binding phosphorylated paratarg and/or a composition containing such an antibody and/or phosphorylated paratarg, or an epitope thereof, and/or a composition containing phosphorylated paratarg. All of these reagents can be in any form described herein, for example peptides and/or proteins may include amino acid substitutions or be conjugated to a reagent as described herein, compositions may contain pharmaceutically suitable substances, et cetera.

Some aspects of this invention relate to methods for screening paraprotein target antigens, including obtaining a pool or pools of sera from patients having or suspected to have gammopathy, contacting said pool or pools of sera with one or more proteins conjugated to or fixed on a solid support, and detecting the selective binding of a paraprotein to any of those one or more proteins.

The use of the foregoing compositions in the preparation of medicaments for treatment of disease, particularly malignant and non-malignant gammopathies, also is provided in accordance with some aspects of the invention.

These and other aspects of the invention, as well as various embodiments thereof, will become more apparent in reference to the drawings and detailed description of the invention.

BRIEF DESCRIPTION OF THE DRAWINGS

FIG. 14: Recombinant paratarg fragments tested for hyperphosphorylation. Hyperphosphorylation occurs between aa 1-25. Method: Indicated fragments of paratarg were amplified by PCR using the primers listed below and full-length paratarg as template followed by cloning in pSfi-FLAG as expression vector. Complementation assays were done as described in the Methods part. As donor lysates LCL extracts of healthy donor and patient were used. Detection was done using anti-FLAG antibody.

```
SLP2-Start-DraI
                                            (SEQ ID NO: 5)
5'-TTT AAA ATG CTG GCG CGC GCG GCG-3'

SLP2-Ende-DraI
                                            (SEQ ID NO: 6)
5'-TTT AAA ACT CAT CTT GAC TCG ATC-3'

SLP2-aa62-DraI-as
                                            (SEQ ID NO: 7)
5'-TTT AAA ACC AGG CTC CAG GAT CCG GTG-3'

SLP2-aa25-DraI-as
                                            (SEQ ID NO: 8)
5'-TTT AAA CGG AGC GCG GCC AGA AGC-3'

SLP2-aa26-DraI-s
                                            (SEQ ID NO: 9)
5'-TTT AAA ATG CGC CGC GCC TCC TCT GGA-3'
```

FIG. 15: Identification of Ser17 as hyperphosphorylation site of paratarg. a) Mutagenisation of paratarg fragment aa1-62. b) IEF analysis. All serines present in paratarg aa1-25 were selectively replaced by ala. Only fragments still containing the 17Ser site showed hyperphosphorylation. Method: site-directed mutagenesis and complementation assays were done as described.

```
                                           (SEQ ID NO: 10)
...11-ALLLR GSLLA SGRAP RRASS GLPRN TVVLF-40...

(SEQ ID NO: 11)
...11-ALLLR GALLA SGRAP RRASS GLPRN TVVLF-40...

(SEQ ID NO: 12)
...11-ALLLR GSLLA AGRAP RRASS GLPRN TVVLF-40...

(SEQ ID NO: 13)
...11-ALLLR GALLA AGRAP RRASS GLPRN TVVLF-40...
```

Figure 16A:
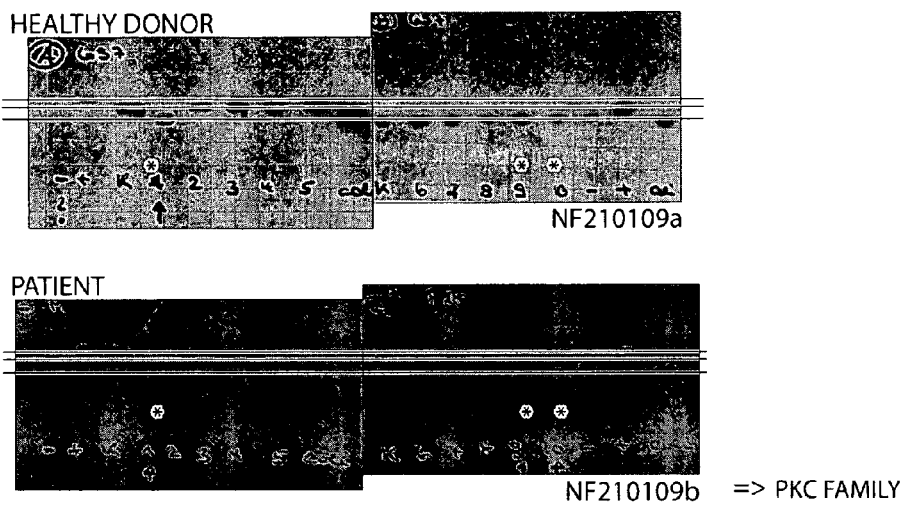

FIG. 16: Identification of the kinase responsible for hyperphosphorylation of Paratarg.

LCLs derived from healthy donors or patients were cultured in the presence of the kinase inhibitors at the indicated concentrations. Lysates were analysed by IEF and immunodetected with anti-STOML2. A shown in this figure, hyperphosphorylation is inhibited by staurosporine, ellagic acid and wortmannin. This indicates that the kinase responsible for the hyperphosphorylation of paratarg is a member of the PKC family. Using BIM_I and Rottlerin, PKC isoform delta or zeta could be identified as responsible for hyperphosphorylation.
  a) Same as b), but with other concentrations of the inhibitors. PKCdelta was excluded
  b) BIM_I (6 µM) and PKCzeta pseudosubstrate clearly identified PKCzeta as the kinase responsible for the hyperphosphorylation of Paratarg.

Figure 17:
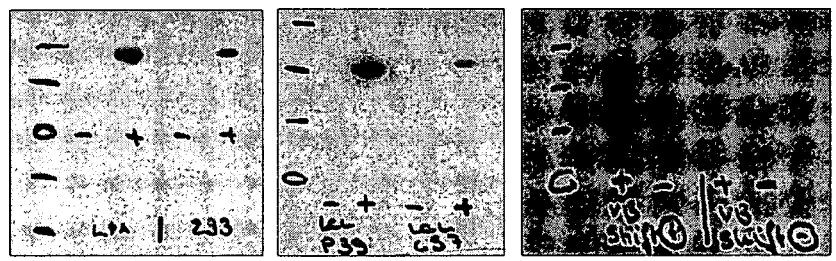

FIG. 17: Coimmunoprecipitation of paratarg and PKCzeta. Left: A direct interaction of these compounds in a cell line which carries hyperphosphorylated paratarg (LP1) and in another one carrying normal paratarg (HEK293) is shown. Middle: Same for LCL derived from patient and healthy control. Right: Same for total blood extract of patient and healthy control.

Figure 18:
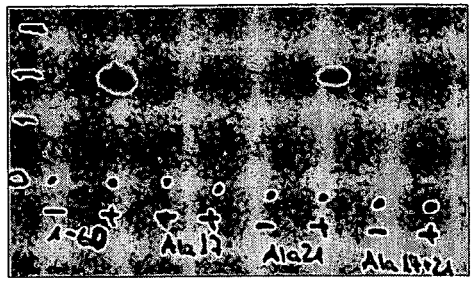
Figure 19A:
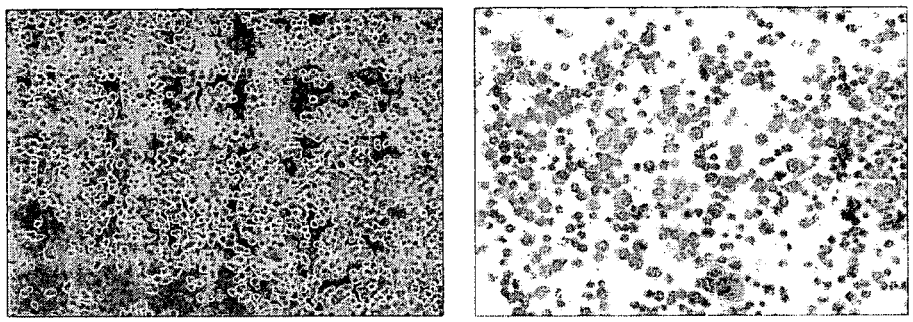
Figure 19B:
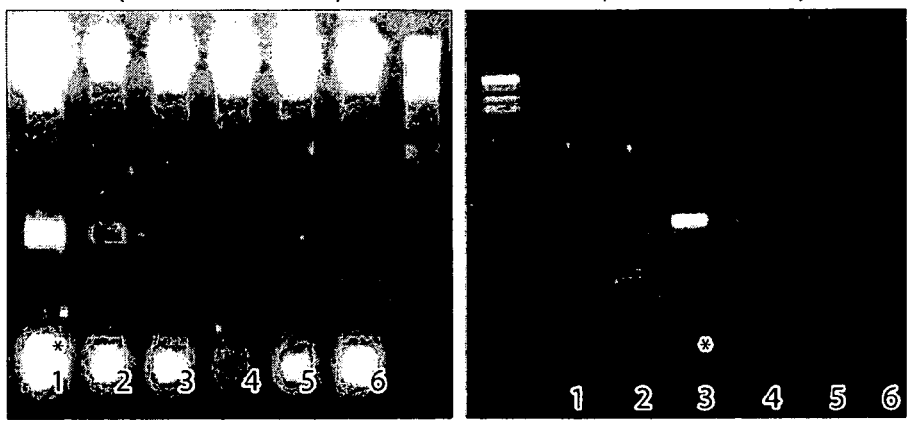
Figure 19C:
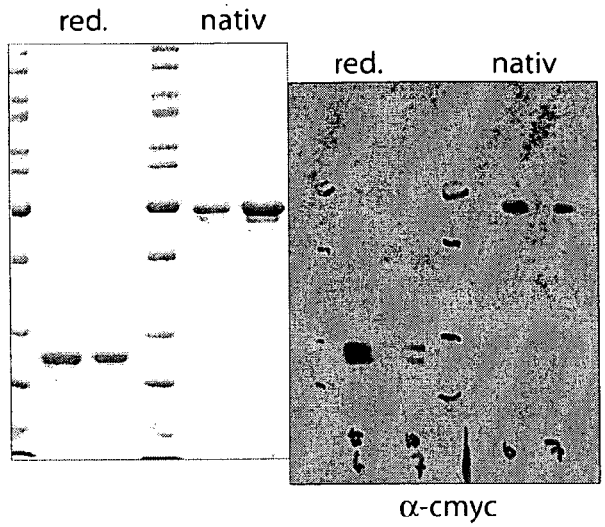
Figure 19D:
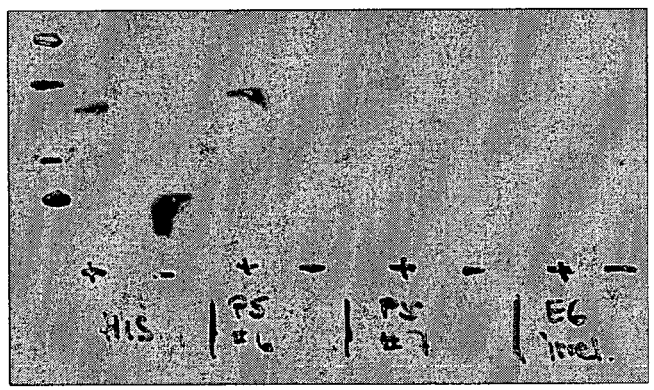
Figure 19E:
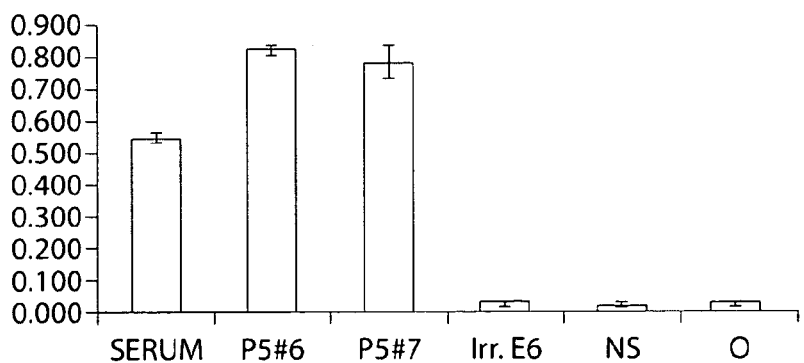
Figure 19F:
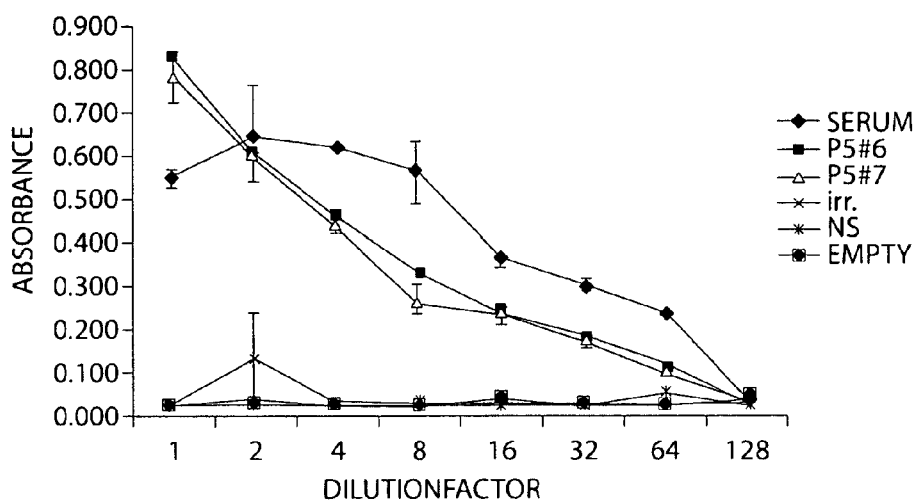

FIG. 18: Direct interaction of 17Ser of paratarg with PKC-zeta. Only fragments still containing 17Ser interact with PKCzeta. No interaction was detected when Ser was replaced by Ala. Methods: Mutagenised recombinant FLAG-tagged paratarg fragments were stably expressed in HEK293 cells. After lysis products were incubated with anti-FLAG and purified using a protein G columns. After gel electrophoresis and blotting, immunodetection was performed using anti-PKC-zeta.

FIG. 19: Cloning, expression and characterization of a B-cell receptor (BCR). Starting from diagnostic bone marrow smears (a), genomic DNA was isolated followed by PCR for amplification of VH and VK (b). For expression these were subcloned in pCES and verified by gel electrophoresis and immunodetection of the His-tag (c). Western blottings showed interaction of the Fab with paratarg while an irrelevant Fab does not (d). In ELISA experiments the recombinant BCR showed similar binding characteristics as patients serum (e,f).

Figure 20A:
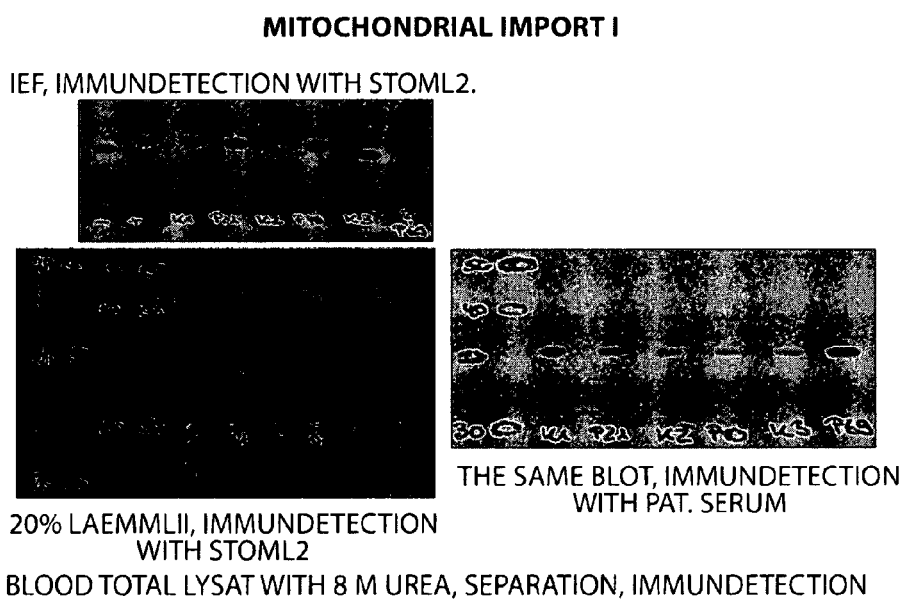
Figure 20B:
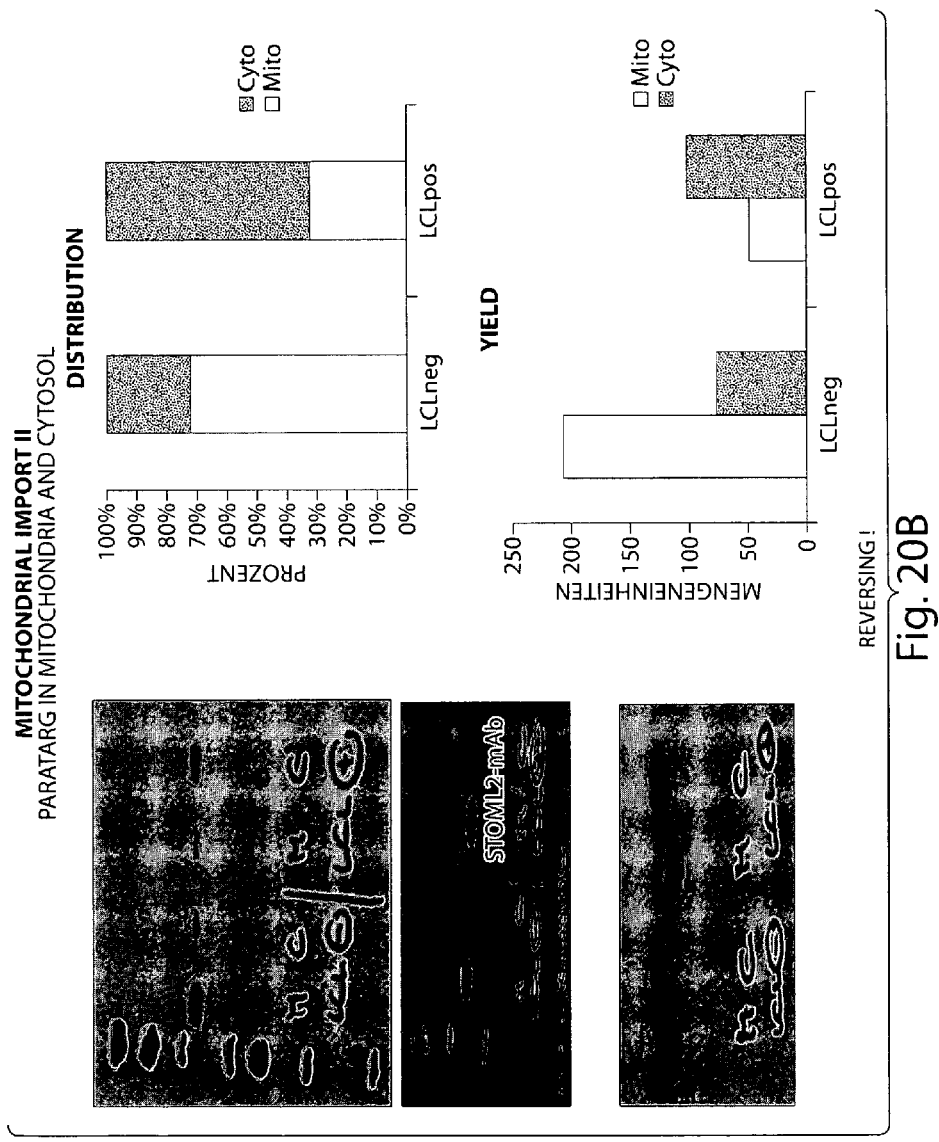

FIG. 20: Mitochondrial import of paratarg. Different amounts of paratarg are imported into mitochondria when comparing healthy donor (GS7) and patient (P39). In both cases a signal sequence is removed during the import process.
a) In a 20% SDS-PAGE 2 bands were detectable representing pre-paratarg and paratarg where the signal was removed (lower left). STOML2-mAb recognized both forms, while patients serum recognizes only the longer paratarg form with signal sequence (right). K represents controls, P represents patients. K1 is one of the 4/200 healthy donors having hyperphosphorylated paratarg but no clinical symptoms of MM/MGUS.
b) This figure shows the import of paratarg into mitochondria of LCL derived from healthy donors or patient LCL. The upper left part represents a 8% SDS-PAGE showing different amounts of paratarg in mitochondria and cytosol, the middle part indicates the purity of the preparation by detection of alpha-cytochrome, the lower left part shows a 20% SDS-PAGE and the different migration of paratarg with and without signal sequence in mitochondria and cytosol. The diagrams show the relative amounts and distribution of paratarg in mitochondria and cytosol. IEF analysis of paratarg in mitochondria and cytosol of LCLs. After import into mitochondria the free signal sequence is not longer hyperphosphorylated.

DETAILED DESCRIPTION OF THE INVENTION

To identify antigenic targets of paraproteins prevalent in malignant and non-malignant gammopathies, for which a causal role in the pathogenesis of these neoplasms has been suggested, we screened a protein macroarray for reactivity with paraproteins in the sera from patients with MGUS and MM. The macroarray consisted of ~37.000 clones derived from a human fetal brain cDNA expression library. Using serum pools of highly diluted paraprotein-containing sera we found 3 clones showing immunoreactivity.

One of these clones is coding for human paratarg (SLP-2, stomatin-like protein 2), an unusual member of the stomatin family. We found that about 15% of all patients (29/192) analyzed showed an immunoreaction of the paraprotein with paratarg at a dilution of $1:10^8$. All paratarg-positive IgG paraproteins were of the IgG3 type (n=24). Specificity was confirmed by absorption studies of the paraprotein from patients' sera, ELISA and bone marrow staining using recombinant paratarg.

Using 2D-gelelectrophoresis, isoelectric focusing and phosphatase treatment we could show that in all patients with a paratarg-specific paraprotein analyzed (14) the paratarg protein is hyperphosphorylated when compared with paratarg protein derived from paratarg immunonegative patients (3) or from healthy donors (120). Two out of 104 anonymous healthy blood donors were also found to have hyperphosphorylated paratarg.

Analyzing patients' families (n=6, in total 18 persons) with respect to paratarg phosphorylation and anti-paratarg antibody titers, all consanguineous relatives of the patient showed hyperphosphorylation of paratarg while non-consanguineous relatives showed normal phosphorylation. None of the family members except one showed serologic signs of MM/MGUS, such as a monoclonal spike in the serum electrophoresis, a band in immunofixation and paratarg ELISA. In one family, two sisters and one brother all carried the hyperphosphorylated paratarg modification, and both sisters had an MGUS with a paraprotein specificity for paratarg.

Our findings provide strong evidence for an involvement of phosphorylated paratarg in the pathogenesis of MGUS/MM by chronic antigenic stimulation. Phosphorylated paratarg, therefore, is useful as a marker of patients at risk for familial MM/MGUS and as the first identified target for specific immunotherapeutic approaches in a significant portion of individuals having MM/MGUS.

These findings allow for more detailed studies on the nature and function of the antigen as well of the kinase/phosphatase responsible for the hyperphosphorylation of paratarg in the respective patients. Together with clinical data these studies will give more insights into pathomechanisms involved in MM/MGUS and lead to novel therapeutic approaches in patients with MM/MGUS.

The term "gammopathy", as used herein, refers to malignant and/or non-malignant gammopathy, if it is not further qualified to refer to a specific type of gammopathy. Multiple myeloma (MM), sclerotic myeloma, Waldenström macroglobulinemia (sometimes also termed "Morbus Waldenström" or "Waldenström disease", WM), immunocytic lymphoma, follicular lymphoma, B cell lymphoma (e.g. immunoblastoma), and chronic B cell lymphocytic leukemia associated with IgM monoclonal proteins, as well as any malignant lymphoma with an associated paraprotein, are non-limiting examples of malignant gammopathies. Benign gammopathies are collectively referred to as gammopathies of undetermined significance (GUS). "A gammopathy" can, accordingly refer to any single malignant or non-malignant gammopathy or any combination of malignant and/or non-malignant gammopathies.

The term "paratarg", as used herein, refers to stomatin-like protein 2 (SLP-2). Human paratarg protein can be found in the database of the National Center for Biotechnology Information (NCBI, online at http://www.ncbi.nlm.nih.gov/) under accession number NP_038470:

```
>gi|7305503|ref|NP_038470.1|stomatin (EPB72)-like 2 [Homo sapiens]
                                                      (SEQ ID NO: 1)
MLARAARGTGALLLRGSLLASGRAPRRASSGLPRNTVVLFVPQQEAWVVERMGRF

HRILEPGLNILIPVLDRIRYVQSLKEIVINVPEQSAVTLDNVTLQIDGVLYLRIMDPYKA

SYGVEDPEYAVTQLAQTTMRSELGKLSLDKVFRERESLNASIVDAINQAADCWGIRC

LRYEIKDIHVPPRVKESMQMQVEAERRKRATVLESEGTRESAINVAEGKKQAQILAS

EAEKAEQINQAAGEASAVLAKAKAKAEAIRILAAALTQHNGDAAASLTVAEQYVSA

FSKLAKDSNTILLPSNPGDVTSMVAQAMGVYGALTKAPVPGTPDSLSSGSSRDVQGT

DASLDEELDRVKMS
```

The gene coding for human paratarg is transcribed into a transcript listed under accession number NM_013442 in the NCBI database:

```
>gi|7305502|ref|NM_013442.1|Homo sapiens stomatin (EPB72)-like 2, cDNA
                                                      (SEQ ID NO: 2)
GGCTTCTGGGAGCGACCGCTCCGCTCGTCTCGTTGGTTCCGGAGGTCGCTGCGGC

GGTGGGAAATGCTGGCGCGCGCGGCGCGGGGCACTGGGGCCCTTTTGCTGAGGG

GCTCTCTACTGGCTTCTGGCCGCGCTCCGCGCCGCGCCTCCTCTGGATTGCCCCGA

AACACCGTGGTACTGTTCGTGCCGCAGCAGGAGGCCTGGGTGGTGGAGCGAATG

GGCCGATTCCACCGGATCCTGGAGCCTGGTTTGAACATCCTCATCCCTGTGTTAG

ACCGGATCCGATATGTGCAGAGTCTCAAGGAAATTGTCATCAACGTGCCTGAGC

AGTCGGCTGTGACTCTCGACAATGTAACTCTGCAAATCGATGGAGTCCTTTACCT

GCGCATCATGGACCCTTACAAGGCAAGCTACGGTGTGGAGGACCCTGAGTATGC

CGTCACCCAGCTAGCTCAAACAACCATGAGATCAGAGCTCGGCAAACTCTCTCTG

GACAAAGTCTTCCGGGAACGGGAGTCCCTGAATGCCAGCATTGTGGATGCCATC

AACCAAGCTGCTGACTGCTGGGGTATCCGCTGCCTCCGTTATGAGATCAAGGATA

TCCATGTGCCACCCCGGGTGAAAGAGTCTATGCAGATGCAGGTGGAGGCAGAGC

GGCGGAAACGGGCCACAGTTCTAGAGTCTGAGGGGACCCGAGAGTCGGCCATCA

ATGTGGCAGAAGGGAAGAAACAGGCCCAGATCCTGGCCTCCGAAGCAGAAAAG

GCTGAACAGATAAATCAGGCAGCAGGAGAGGCCAGTGCAGTTCTGGCGAAGGCC

AAGGCTAAAGCTGAAGCTATTCGAATCCTGGCTGCAGCTCTGACACAACATAAT

GGAGATGCAGCAGCTTCACTGACTGTGGCCGAGCAGTATGTCAGCGCGTTCTCCA

AACTGGCCAAGGACTCCAACACTATCCTACTGCCCTCCAACCCTGGCGATGTCAC

CAGCATGGTGGCTCAGGCCATGGGTGTATATGGAGCCCTCACCAAAGCCCCAGT

GCCAGGGACTCCAGACTCACTCTCCAGTGGGAGCAGCAGAGATGTCCAGGGTAC

AGATGCAAGTCTTGATGAGGAACTTGATCGAGTCAAGATGAGTTAGTGGAGCTG

GGCTTGGCCAGGGAGTCTGGGGACAAGGAAGCAGATTTTCCTGATTCTGGCTCTA

GCTTCCCTGCCAAGATTTTGGTTTTTATTTTTTATTTGAACTTTAGTCGTGTAATA

AACTCACCAGTGGCAAACCTGAAAAAAAAAAAAAAAAAAAAAAAAAA
```

Paratarg (SLP-2) is a novel and unusual stomatin homolog of unknown function. It has been implicated in interaction with erythrocyte cytoskeleton and presumably other integral membrane proteins, but not directly with the membrane bilayer. Paratarg has been suggested to be involved in human esophageal squamous cell carcinoma (ESCC), lung cancer, laryngeal cancer, and endometrial adenocarcinoma and the effects of SLP-2 on ESCC cells (Zhang et al, 2006).

Figure 9:
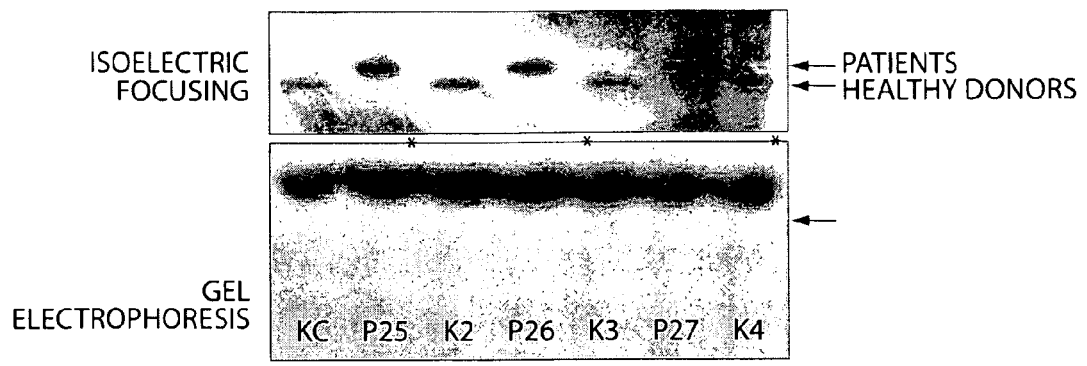
FIG. 9 illustrates paratarg specific immunodetection in patients with paratarg-reactive paraproteins (P25, P26), paratarg non-reactive patient (P27) and healthy donors (K1, K2, K3). In the lower part gel electrophoresis according Laemmli is shown while in the upper part isoelectric focusing is shown. After the separation indicated, the samples were transferred on PVDF membrane and immunodetected as described in methods.
Figure 10:
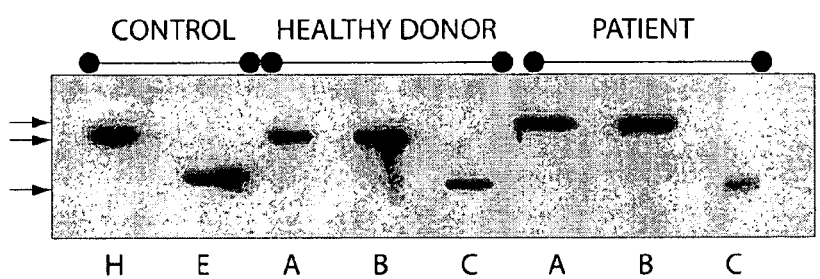
FIG. 10 demonstrates dephosphorylation of paratarg derived from patients and healthy donors. Shown is an IEF separation followed by immunodetection with anti-Paratarg as described in methods. A: erythrocyte lysate; B: erythrocyte lysate incubated as in C, but without enzyme; C: erythrocyte lysate incubated with alkaline phosphatase overnight at 37° C. H represents paratarg expressed in HEK293, E represents paratarg expressed in *E. coli*. The arrows indicate the 3 forms of paratarg phosphorylation.

Paratarg is subject to protein phosphorylation, in which at least one amino acid residue of paratarg is phosphorylated. As is known in the art, examples of amino acid residues amenable to phosphorylation include, but are not limited to, serine, threonine, tyrosine, and histidine. The terms "phosphorylated paratarg" and "hyperphosphorylated paratarg" as used herein, refer to paratarg in which at least one of the amino acid residues 17-31 are phosphorylated, particularly serine 17 ("17Ser") and which is represented by a band/signal obtained by IEF and immunodetection as shown in FIGS. 9 and 10. Well known to those skilled in the art, protein phosphorylation can be mimicked by substitution of one or more amino acid residue/s with one or more residue/s that mimic/s the original amino acid residue/s in its/their phosphorylated state. Non-limiting examples of such amino acid residues that are able to mimic protein phosphorylation include aspartate, aspartic acid, glutamate, glutamic acid and phenylalanine. The term "phosphorylated paratarg" as used herein is meant to also refer to paratarg protein/s, or epitope/s thereof, in which one or more amino acid residue/s amenable to phosphorylation has/have been substituted with one or more residue/s that mimic/s the original amino acid residue/s in its/their phosphorylated state.

Paratarg shows homology to other stomatin family proteins. As used herein, the term "homology" qualifies the degree of similarity between sequences of amino acids or nucleotides. Homology of two or more such sequences can be determined by alignment of such sequences, preferably by using a computer program specifically designed for this purpose.

Optimal alignment of sequences for comparison may be conducted using programs such as BLAST, publicly available on the National Library of Medicine website. Other programs such as UniGene (The National Library of Medicine website), SAGE Anatomic Reviewer and its Virtual Northern tool, (The Cancer Genome Anatomy Project CGAP website) are also publicly available. Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

The term "epitope", as used herein, refers to a part of a macromolecule. This part is recognized by the immune system, specifically by antibodies, B cells, or T cells. This part is also known as the antigenic determinant.

In general, preferred epitopes or variants of paratarg typically will share less than 70% nucleotide and/or less than 80% amino acid identity to the sequences of other stomatin family member polypeptides.

Examples of preferred paratarg epitopes include, but are not limited to, polypeptides comprising amino acid residues 1-40 or 237-356 of NP_038470 (SEQ ID NO: 1). Examples of more preferred paratarg epitopes include, but are not limited to, polypeptides comprising amino acid residues 17-31 of NP_038470 (SEQ ID NO: 1). Polypeptides comprising five, six, seven, eight or more contiguous amino acids of amino acid residues 17-31 of NP_038470 (SEQ ID NO: 1) are also examples of more preferred paratarg epitopes. Examples of more preferred paratarg epitopes further include, but are not limited to polypeptides comprising amino acid residues 17-25 of NP_038470 (SEQ ID NO: 1). As used in relation to paratarg epitopes, the term "fragment" of a given amino acid sequence is meant to refer to all polypeptides that comprise a part of the given amino acid sequence. Accordingly, a paratarg epitope comprising a fragment of a given amino acid sequence, refers to any molecule that comprises said fragment and can specifically bind to a paratarg-directed paraprotein. This includes, as non-limiting examples, polypeptides comprising such a paratarg epitope, polypeptides that comprise such an epitope in addition to other amino acid sequences (e.g., wherein the epitope is fused to an additional amino acid sequence at either or both ends of the epitope), and polypeptides comprising an amino acid substitution and/or a modified peptide bond as described herein. In preferred embodiments, the fragment comprises at least 5, at least 6, at least 7 or at least eight amino acids. For instance, polypeptides comprising amino acids 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 17-21, 17-22, 17-23, 17-24, 17-25, 17-26, 17-27, 17-28, 17-29, 17-30, 17-31, 17-32, 17-33, 17-34, 17-35, 17-36, 17-37, 17-38, 17-39, 17-40, 18-40, 19-40, 20-40, 21-40, 22-40, 23-40, 24-40, 1-50, 1-100, 1-200, 1-300, or 1-365 of NP_038470 (SEQ ID NO: 1) would be non-limiting examples of polypeptides comprising a fragment of amino acid residues 17-25 of NP_038470 (SEQ ID NO: 1)".

Some embodiments of the invention involve the use of binding agents. Such binding agents can be used in methods of the invention including the diagnosis and/or treatment of MM or MGUS.

Binding agents according to some aspects of the present invention may be used to inhibit the native activity of cells expressing phosphorylated paratarg or paraprotein/s binding phosphorylated paratarg and/or the level and/or the biological activity of phosphorylated paratarg or paraprotein/s binding phosphorylated paratarg, for example, by binding to any of these proteins.

In preferred embodiments of this invention, binding agents are isolated polypeptides. In some preferred embodiments, the binding agent is an isolated antibody, or antigen-binding fragment thereof, which specifically binds phosphorylated paratarg or paraprotein/s binding phosphorylated paratarg. In some embodiments, the binding polypeptide is isolated paratarg, or an epitope thereof, selectively binding paraproteins. In some preferred embodiments, the binding polypeptide is isolated phosphorylated paratarg, or an epitope thereof, selectively binding paraprotein/s.

Preferably, isolated polypeptides according to some aspects of this invention, for example antibodies and antigen-binding fragments thereof, or isolated phosphorylated paratarg and epitopes thereof, are selected from the group consisting of peptides comprising D-amino acids, peptides comprising at least one -psi[CH$_2$NH]-reduced amide peptide bond, peptides comprising at least one -psi[COCH$_2$]-ketomethylene peptide bond, peptides comprising at least one -psi[CH(CN)NH]-(cyanomethylene)amino peptide bond, peptides comprising at least one -psi[CH$_2$CH(OH)]-hydroxyethylene peptide bond, peptides comprising at least one -psi[CH$_2$O]-peptide bond, and peptides comprising at least one -psi[CH$_2$S]-thiomethylene peptide bond.

Binding agents according to some aspect of this invention can be used in assays to detect the presence or absence of phosphorylated paratarg or paraprotein/s and in purification protocols to isolate cells expressing phosphorylated paratarg or paraprotein/s.

According to some aspects of this invention, binding agents can be used to selectively target drugs, toxins or other molecules (including detectable diagnostic molecules) to cells which express phosphorylated paratarg or paraprotein/s binding phosphorylated paratarg. For example, plasma cells that express paraprotein/s binding phosphorylated paratarg can be treated with cytotoxic compounds that are selective for paraprotein/s binding phosphorylated paratarg.

Binding agents according to some aspects of this invention can be used to inhibit the native biological activity of phosphorylated paratarg or paraprotein/s binding phosphorylated paratarg, for example, to treat a subject or to further characterize the functions of these molecules.

In preferred embodiments of this invention, binding agents can be used to decrease the level of paraprotein/s binding phosphorylated paratarg in a body fluid.

Antibodies, or antigen-binding fragments thereof, as provided by some aspects of the present invention, can be prepared by any of a variety of methods, including administering a protein, fragments of a protein, cells expressing the protein or fragments thereof and the like to an animal to induce polyclonal antibodies.

The production of monoclonal antibodies is well known in the art.

As detailed herein, antibodies may be used, for example, to determine the level of phosphorylated paratarg or paraprotein/s binding phosphorylated paratarg in a body fluid, to identify cells expressing phosphorylated paratarg or paraprotein/s binding phosphorylated paratarg, or to remove a portion of paraprotein/s binding phosphorylated paratarg from a subjects body fluid.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab') fragment (or F(ab')2 fragment), retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Figure 13:
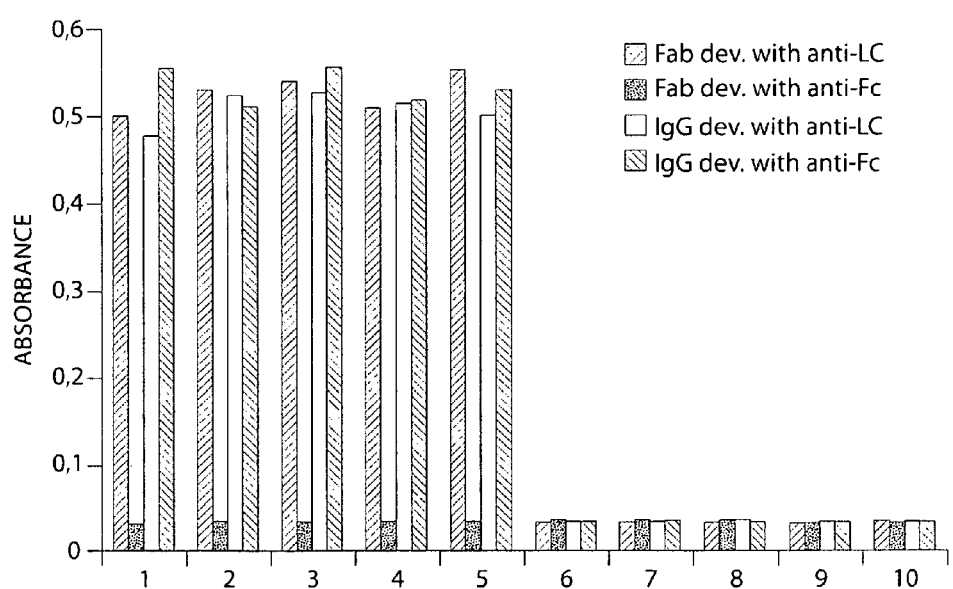
FIG. 13: F(ab') derived from serum by purification of paratarg specific IgG followed by papain digestion shows identical binding as the complete IgG while the Fc part does not bind. The figure displays paratarg-ELISAs using patients' sera or corresponding Fab-fragments. Development was done using secondary antibodies specific for a) light chains (LC) or b) Fc. Lanes 1-5: paratarg-positive sera. lanes 6-8: paratarg-negative sera. lanes 9, 10: healthy control sera. Sera containing IgG$_3$-paraproteins were purified by ProtA- and ProtG-beads followed by digestion with papain (10 µg/ml, 2.5 h, 37° C.) in presence of 0.1 mM cysteine. After inactivation with iodoacetamide the supernatant containing the Fab fragments was dialyzed against PBS, concentrated, checked by PAGE and western blotting, and used in ELISA. In each group, the left bar represents F(ab') developed with anti-LC, the second bar from the left represents F(ab') developed with anti-Fc, the third bar from the left represents IgG developed with anti-LC, and the right bar represents IgG developed with anti-Fc.

F(ab') fragments derived from serum by purification of paratarg specific IgG followed by papain digestion shows identical binding as the complete IgG while the Fc part does not bind. (FIG. 13)

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford) In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205. Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab'), Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab') fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. In some embodiments, the present invention provides so-called single chain antibodies (e.g., ScFv), (single) domain antibodies, and other intracellular antibodies. Domain antibodies, camelid and camelized antibodies and fragments thereof, such as those described in patents and published patent applications of Ablynx NV and Domantis also can be used as described herein.

Paratarg or phosphorylated paratarg can be obtained from one or more subjects known to express it. Alternatively, paratarg, or epitopes thereof, can be expressed in a suitable host organism and isolated from a culture of such a host organism expressing the desired polypeptide. Post translational modifications, for example phosphorylation, can be introduced in vitro or in vivo. Alternatively, a modified protein can be expressed in which one or more amino acid residue/s amenable to phosphorylation is/are substituted with one or more amino acid residue/s mimicking the original residue/s in its/ their phosphorylated state. Methods of generating suitable cultures of host organisms expressing the desired polypeptides are well known to those of skill in the art of protein expression.

Thus, some embodiments of the invention involve polypeptides of numerous size and type that bind specifically to phosphorylated paratarg or to paraprotein/s binding phosphorylated paratarg.

Polypeptides according to some aspects of the invention may be derived from other sources as well. For example, polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

Binding agents according to some aspects of this invention can be used, for example, in screening assays to detect the presence or absence of phosphorylated paratarg or paraprotein/s binding phosphorylated paratarg. Binding agents according to some aspects of this invention can be used, for example, in quantitative assays, for example, to determine the level of phosphorylated paratarg or paraprotein/s binding phosphorylated paratarg in biological samples, such as body fluid, tissue or cell samples.

As used herein, the term "body fluid" is meant to refer to one or more fluids a subject's body comprises or produces. Accordingly, examples of body fluids include, but are not limited to, blood, serum, lymph, saliva, urine, or cerebrospinal fluid, and the like. A body fluid sample may include cells and/or fluid. A body fluid, tissue or cell sample may be obtained from a subject and the cells that may be included in said sample may be grown in culture (for example as a cell line) before being processed further according to any of the embodiments of the invention. A body fluid, tissue or cell sample can be obtained from a subject using methods well-known to those of ordinary skill in the related medical arts.

As used herein, a "subject" is preferably a human, non-human primate, or other mammal, for example a cow, horse, pig, sheep, goat, dog, cat or rodent. In all embodiments, human subjects are preferred.

In some cases, the binding agents, for example the antibodies of the invention, are labeled with or coupled to or conjugated with detectable molecules, preferably fluorescent molecules, or magnetic entities, such as magnetic particles. As used herein, the terms "labeled with" and "conjugated with" are intended to refer to, but not to be limited to, two or more molecules, at least one of them preferably being a polypeptide, bound to each other by one or more of the following: one or more covalent bonds, one or more ionic-bonds, one or more permanent dipole bonds, one or more instantaneous dipole to induced dipole bonds (van der Waals). Molecules or entities as provided by some embodiments of the invention can be used to facilitate detection and/or separation of the cells expressing phosphorylated paratarg or paraprotein/s binding phosphorylated paratarg from other cells of a cell population. As such, cells expressing phosphorylated paratarg or paraprotein/s binding phosphorylated paratarg can be isolated by a variety of methods known in the art, preferably, for example, by methods such as fluorescence-activated cell sorting (FACS) and magnetic activated cell sorting (MACS).

According to some aspects of this invention, isolated cells or cell populations expressing one or more paraprotein/s binding phosphorylated paratarg, for example plasma cells, can be used to develop one or more antibodies using methods well known to those of skill in the art, for example by generating a cell line producing such antibodies. According to some aspects of this invention, isolated cells or cell populations expressing phosphorylated paratarg can be used to produce phosphorylated paratarg, for example by generating a cell line expressing phosphorylated paratarg.

Examples of diagnostic methods based on identification and characterization of cells expressing phosphorylated paratarg or paraprotein/s binding phosphorylated paratarg include, but are not limited to, identifying the presence of cells expressing phosphorylated paratarg or paraprotein/s binding phosphorylated paratarg in a subject in vivo, ex vivo or in vitro. In vivo methods may include administering to the subject a detectably labeled binding agent that binds to phosphorylated paratarg or paraprotein/s binding phosphorylated paratarg.

For ex vivo or in vitro methods, a body fluid, tissue or cell sample suspected of containing phosphorylated paratarg or paraprotein/s binding phosphorylated paratarg or cells expressing phosphorylated paratarg or paraprotein/s binding phosphorylated paratarg can be contacted with a detectably labeled agent selectively binding to phosphorylated paratarg or paraprotein/s binding phosphorylated paratarg. Binding of the detectably labeled agent indicates the presence of cells expressing phosphorylated paratarg or paraprotein/s binding phosphorylated paratarg in the sample, and can be detected by methods well known to those of skill in the art.

Some aspects of the invention relate to diagnosing or monitoring a gammopathy in a subject by determining the presence or amount or level of phosphorylated paratarg or paraprotein/s binding phosphorylated paratarg.

In preferred embodiments, this determination is performed by assaying a body fluid sample obtained from a subject for the presence of phosphorylated paratarg or paraprotein/s binding phosphorylated paratarg as described herein.

The presence or level of phosphorylated paratarg or paraproteins specifically binding phosphorylated paratarg may be determined using routine methods known to those of ordinary skill in the art. Examples of preferred methods include, but are not limited to, immunologically based assay methods from the list of immunohistochemistry, western blotting assay, enzyme-linked immunosorbent assay (ELISA), enzyme-linked immunospot assay (ELISPOT), lateral flow test assay, enzyme immunoassay (EIA), fluorescent polarization immunoassay (FPIA), chemiluminescent immunoassay (CLIA), antibody sandwich capture assay, or isoelectric focusing (IEF) assay.

Some methods of determining the presence and/or level of phosphorylated paratarg or paraprotein/s binding phosphorylated paratarg in body fluid or tissue samples may include use of labels to monitor the presence of cells expressing phosphorylated paratarg or paraprotein/s binding phosphorylated paratarg. Examples of labels include, but are not limited to fluorescent labels, radiolabels or chemiluminescent labels, which may be utilized to determine whether phosphorylated paratarg or paraprotein/s binding phosphorylated paratarg is expressed in a body fluid, cell or tissue, and/or to determine the level of expression in the body fluid, cell or tissue. For example, as described elsewhere herein, a fluorescently labeled or radiolabeled antibody that selectively binds to phosphorylated paratarg or paraprotein/s binding phosphorylated paratarg may be contacted with a body fluid, tissue or cell to visualize the polypeptide in vitro or in vivo. These and other in vitro and in vivo imaging methods for determining the presence and/or level of phosphorylated paratarg or paraprotein/s binding phosphorylated paratarg in body fluid or tissue samples or the presence of cells expressing phosphorylated paratarg or paraprotein/s binding phosphorylated paratarg are well known to those of ordinary skill in the art.

Paratarg and/or phosphorylated paratarg can be detected by standard methods known to those of skill in the art. Antibodies useful for the detection of paratarg and/or phosphorylated paratarg can be obtained from commercial vendors, for example under catalog number 612471 from Becton Dickinson. Measurement of phosphorylated paratarg or paraprotein/s binding phosphorylated paratarg in a subject over time by sequential determinations permits monitoring of a gammopathy and/or the effects of a course of treatment. For example, a body fluid sample may be obtained from a subject, tested for the existence or quantity of phosphorylated paratarg or paraprotein/s binding phosphorylated paratarg and at a second, subsequent time, another body fluid sample may be obtained from the subject and similarly tested. The results of the first and second (or subsequent) tests can be compared as a measure of the onset, regression or progression of a gammopathy, or, if treatment was undertaken during the interval between obtaining the samples, the effectiveness of the treatment may be evaluated by comparing the results of the two tests.

It is expected that a typical body fluid sample from a patient not having a gammopathy will have zero or a very low level of phosphorylated paratarg or paraprotein/s binding phosphorylated paratarg, whereas a body fluid sample from a patient having a paratarg-positive gammopathy will have a significantly higher level of phosphorylated paratarg or paraprotein/s binding phosphorylated paratarg, which can be termed an "aberrant level" of phosphorylated paratarg or paraprotein/s binding phosphorylated paratarg. The relative levels of phosphorylated paratarg or paraprotein/s binding phosphorylated paratarg in body fluid samples of gammopathy negative patients versus those of patients having a paratarg positive gammopathy are shown in the examples below. As used herein, the term "aberrant level" is intended to refer to any level of phosphorylated paratarg or paraprotein/s binding phosphorylated paratarg that is different by a statistically significant amount from the expected level of phosphorylated paratarg or paraprotein/s binding phosphorylated paratarg.

For example, the presence of phosphorylated paratarg or paraprotein/s binding phosphorylated paratarg in a body fluid or tissue that is not expected to have such expression would be an example of an "aberrant level" of phosphorylated paratarg or paraprotein/s binding phosphorylated paratarg. Likewise, a significantly higher level of phosphorylated paratarg or paraprotein/s binding phosphorylated paratarg than expected is another example of an "aberrant level" of phosphorylated paratarg or paraprotein/s binding phosphorylated paratarg. Therefore, a determination of the level of phosphorylated paratarg or paraprotein/s binding phosphorylated paratarg is diagnostic of a paratarg-positive gammopathy if the level of expression is above a control, or reference, or baseline level determined for that body fluid or tissue type.

The control, or reference, or baseline level can be determined using standard methods known to those of skill in the art. Examples of standard methods include, for example, assaying a number of body fluid or tissue samples from subjects that are clinically normal in respect to the disease to be tested for (e.g., do not have clinical signs of a gammopathy in that body fluid or tissue type) and determining the mean level of phosphorylated paratarg or paraprotein/s binding phosphorylated paratarg for the samples.

The level of phosphorylated paratarg or paraprotein/s binding phosphorylated paratarg can indicate a paratarg positive gammopathy if the level of phosphorylated paratarg or paraprotein/s binding phosphorylated paratarg is significantly higher in the body fluid or tissue or cell sample than in a control sample, e.g. a negative control sample. In some embodiments, the level of expression of phosphorylated paratarg or paraprotein/s binding phosphorylated paratarg in the body fluid or tissue or cell sample being examined is at least about 5%, about 10%, 10-50%, about 20%, about 30%, about 40%, about 50%, 50-100%, about 60%, about 70%, about 80%, about 90%, about 100%, 100-150%, about 150%, 150-200%, about 200%, 200-250%, about 250%, 250-500%, about 300%, about 400%, about 500%, 500-1000%, about 1000%, 1000-2500%, about 1500%, about 2000%, about 2500%, about 3000%, about 4000%, about 5000%, 5000%-10000%, about 6000%, about 7000%, about 8000%, about 9000%, or about 10000%, or more, greater than the level of phosphorylated paratarg or paraprotein/s binding phosphorylated paratarg in negative control body fluid or tissue or cell samples, indicating a paratarg positive gammopathy, for example paratarg positive MM and/or MGUS, in the subject the body fluid or tissue or cell sample of which is being examined.

Some aspects of this invention relate to the detection of phosphorylated paratarg or paraprotein/s binding phosphorylated paratarg in a body fluid or organ donated by a subject, for example for subsequent administration, transfer, or transplantation to a recipient. In some embodiments, the donated body fluid, for example, peripheral blood, or organ, for example, bone marrow, kidney, liver, or heart, are tested for phosphorylated paratarg or paraprotein/s binding phosphorylated paratarg, for example, by performing any diagnostic method provided by aspects of this invention. In some embodiments, the donor of the body fluid or organ is tested in temporal proximity to the donation, for example, prior, during, or subsequent to the donation, for phosphorylated paratarg or paraprotein/s binding phosphorylated paratarg. For example, in some embodiments, the subject is a blood donor and a sample of the donated blood is obtained and tested, or the donor is tested by obtaining a body fluid, tissue, or cell sample in temporal proximity to the blood donation, for example, prior, during, or subsequent to the blood donation. In some embodiments, the subject is an organ donor and a sample of the organ is obtained and tested, or the donor is tested by obtaining a body fluid, tissue, or cell sample in temporal proximity to the organ donation, for example, prior, during, or subsequent to the organ donation. In some embodiments, the subject is a donor of a body fluid, for example, a blood donor, or an organ donor, and determination of a level of phosphorylated paratarg or paraprotein/s binding phosphorylated paratarg in a body fluid, or tissue, or cell sample of the donor is determined prior to administration, transfer, or transplantation of the donated body fluid (e.g., blood) or organ to a recipient. In some embodiments, if an elevated level of phosphorylated paratarg or paraprotein/s binding phosphorylated paratarg, for example, as compared to a reference or control level representative of donors not having a gammopathy, is detected in a body fluid, tissue, or cell sample of the donor, and/or if the donor of the body fluid or organ is indicated to have a gammopathy, for example, by the result of any diagnostic method provided by some aspects of this invention, then the donated body fluid or organ is disqualified from administration, transfer, or transplantation to a recipient. In some embodiments, if no elevated level of phosphorylated paratarg or paraprotein/s binding phosphorylated paratarg, for example, as compared to a reference or control level representative of donors not having a gammopathy, is detected in a body fluid, tissue, or cell sample of the donor, and/or if the donor of the body fluid or organ is indicated not to have a gammopathy, for example, by the result of any diagnostic method provided by some aspects of this invention, then the donated body fluid or organ is qualified for administration, transfer, or transplantation to a recipient. In some embodiments, a donated body fluid or organ is only qualified for transplantation, if the level of phosphorylated paratarg or paraprotein/s binding phosphorylated paratarg detected in a body fluid, tissue, or cell sample of the donor is not substantially different from a control or reference level, and/or if the donor is indicated not to have a gammopathy by any diagnostic method provided by some aspects of this invention. In some embodiments, the donated body fluid is blood and a level of phosphorylated paratarg or paraprotein/s binding phosphorylated paratarg is determined in a sample of the donated blood before the blood is administered to a recipient. In some embodiments, donated blood is only administered to a recipient subsequent to a determination of a level of phosphorylated paratarg or paraprotein/s binding phosphorylated paratarg, and only if that level is not substantially different from a control or reference level, for example, a level representative of blood donors not having a gammopathy. In some embodiments, a donated body fluid or organ disqualified from administration, transfer, or transplantation to a recipient based on a detection of phosphorylated paratarg or paraprotein/s binding phosphorylated paratarg is labeled in a way indicating its disqualification and/or destroyed. In some embodiments, a donated body fluid or organ qualified for administration, transfer, or transplantation to a recipient based on a detection of phosphorylated paratarg or paraprotein/s binding phosphorylated paratarg is labeled in a way indicating its qualification and/or administered, transferred, or transplanted to a recipient.

In some embodiments, the invention provides kits for assaying the presence and/or level of phosphorylated paratarg or paraprotein/s binding phosphorylated paratarg, preferably comprising antibodies that specifically bind to phosphorylated paratarg or paraprotein/s binding phosphorylated paratarg, and/or paratarg or a paraprotein-binding epitope thereof An example of such a kit may include one or more antibodies, or antigen-binding fragments thereof, specifically binding to phosphorylated paratarg or paraprotein/s binding phosphorylated paratarg. The one or more antibodies, or antigen-binding fragment thereof, may be applied to a body fluid or tissue or cell sample from a subject diagnosed with, suspected of having, or believed to be free of a gammopathy and the sample may then be processed to assess whether specific binding occurs between the antibody and phosphorylated paratarg or paraprotein/s binding phosphorylated paratarg . As will be understood by one of skill in the art, binding assays may also be performed with a sample or object contacted with an antibody and/or phosphorylated paratarg or paraprotein/s binding phosphorylated paratarg that is in solution, for example in a 96-well plate or applied directly to an object surface.

As an option, a kit according to some embodiments of the invention may include one or more control samples. As used herein the term "control sample" typically means a sample tested in parallel with the experimental materials, although a control sample may be tested separately from experimental materials, and may be a historical control value. Examples of control samples include, but are not limited to, samples from control body fluid and samples generated through manufacture to be tested in parallel with the experimental samples.

In some embodiments, a kit may include a positive control sample and/or a negative control sample. Typically the negative control will be based on apparently healthy individuals in an appropriate age bracket. A positive control, for example based on individuals indicated as having paratarg-positive gammopathy or generated through manufacture can be used to verify experimental procedures. Alternatively, a positive control can comprise isolated paratarg or isolated paraprotein selectively binding isolated paratarg.

The foregoing kits can include instructions or other printed material on how to use the various components of the kits for diagnostic purposes.

The invention provides for treatment of a subject having or suspected of having a paratarg positive gammopathy comprising killing or inhibiting proliferation of cells expressing phosphorylated paratarg or paraprotein/s binding phosphorylated paratarg. The terms "therapy", "therapeutic", "treat" or "treatment" refer to, but are not limited to, one or more clinical intervention with an intent to prevent, ameliorate, or cure a condition or symptoms of the condition in a subject.

In preferred embodiments, the treatment is aimed to induce a decrease of the level of phosphorylated paratarg or protein/s binding phosphorylated paratarg in a subject. Apparent to those skilled in the relevant medical arts, this can be accomplished by various approaches including, but not limited to, depleting, completely or in part, protein/s binding phosphorylated paratarg from a body fluid, or removing killing or inhibiting the proliferation of cells expressing phosphorylated paratarg or protein/s binding phosphorylated paratarg. Suitable methods are apparent to those of skill in the relevant medical art. One example of a suitable method is apheresis, comprising passing a body fluid (for example, blood) of a subject through an apparatus separating out one or more particular constituents of the body fluid, (for example, specific cells or proteins) and returning the body fluid to the subject. According to some aspects of the invention, this apparatus could comprise one or more of the binding agents described herein bound to a solid support or otherwise restrained to the apparatus. In some aspects, these agents could selectively bind proteins binding phosphorylated paratarg or protein/s binding phosphorylated paratarg or cells expressing at least one of any of these proteins when contacted with a body fluid containing them. As a result, these constituents would thus be removed, in full or in part from said body fluid. Other suitable methods will be apparent to those of skill in the art, as this invention is not limited in this respect. In preferred embodiments, treatment is aimed at reducing or inhibiting a native activity of phosphorylated paratarg or protein/s binding phosphorylated paratarg in a subject, for example by binding them.

A treatment according to some aspects of this invention can be a monotherapy, for example treating a subject only by using one or more methods and/or compositions described herein to decrease the level of phosphorylated paratarg or paraprotein/s binding phosphorylated paratarg or to reduce or inhibit a native activity of phosphorylated paratarg or paraprotein/s binding phosphorylated paratarg. However, the treatment also can be an adjunct therapy to one or more other therapies, for example immune therapies, radiation therapies, and/or chemotherapies. Aspects of these methods are described in greater detail elsewhere herein.

Some methods for depleting, completely or in part, protein/s binding phosphorylated paratarg from a body fluid, according to some embodiments of this invention, feature the use of binding agents, as described elsewhere herein, bound to a solid support. A body fluid from a subject can be contacted with this support-bound binding agent under conditions that allow for the selective binding of the binding agent and the paraprotein/s binding phosphorylated paratarg. The bound fraction of paraprotein/s binding phosphorylated paratarg can subsequently be separated from the body fluid and the body fluid, now with a decreased amount of paraprotein/s binding phosphorylated paratarg can be returned to the subject. This method is well known as apheresis to those of skill in the medical arts.

Some methods for killing or inhibiting the proliferation of cells expressing phosphorylated paratarg or paraprotein/s binding phosphorylated paratarg, according to some embodiments of this invention, feature contacting a cell population containing such cells with an agent or combination of agents selectively targeted to cells expressing phosphorylated paratarg or paraprotein/s binding phosphorylated paratarg.

By "selectively targeted" is meant that the agent or combination of agents selectively recognizes and binds to cells expressing phosphorylated paratarg or paraprotein/s binding phosphorylated paratarg as compared to non-expressing cells in a tissue or cell population. The agent or combination of agents can effectively kill the cells expressing phosphorylated paratarg or paraprotein/s binding phosphorylated paratarg or inhibit their proliferation by one of several mechanisms, such as by induction of apoptosis, bringing into close proximity a cytotoxic or cytostatic agent, or attracting other cells such as cytotoxic T lymphocytes or macrophages that can kill or inhibit proliferation of the targeted cells. By "cytotoxic or cytostatic agent" is meant an agent (for example a molecule) that kills or reduces proliferation of cells.

The binding agents of the present invention can be used to therapeutically target cells expressing phosphorylated paratarg or paraprotein/s binding phosphorylated paratarg. In a preferred embodiment, antibodies can be used as binding agents to target phosphorylated paratarg or paraprotein/s binding phosphorylated paratarg. In some preferred embodiments, phosphorylated paratarg, or epitopes thereof, can be used as binding agents. These binding agents can be linked not only to a detectable marker but also to a cytotoxic agent or an immunomodulator. Some examples of cytotoxic agents include, but are not limited to, cytotoxic radionuclides, chemical toxins, chemotherapeutic agents and protein toxins.

The cytotoxic radionuclide or radiotherapeutic isotope preferably is an alpha-emitting isotope such as 225Ac, 211At, 212Bi, 213Bi, 212Pb, 224Ra or 223Ra. Alternatively, the cytotoxic radionuclide may a beta-emitting isotope such as 186Rh, 188Rh, 177Lu, 90Y, 131I, 67Cu, 64Cu, 153Sm or 166Ho. Further, the cytotoxic radionuclide may emit Auger and low energy electrons and may be one of the isotopes 125I, 123I or 77Br.

Examples of suitable chemical toxins or chemotherapeutic agents include, but are not limited to, members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Examples of antineoplastic agents that may be conjugated to the binding agents of the present invention include, but are not limited to, dolastatins (U.S. Pat. Nos. 6,034,065 and 6,239,104) and derivatives thereof. Of particular interest is dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., Anticancer Drug Des. 13(4):243-277, 1998; Woyke, T. et al., Antimicrob. Agents Chemother. 45(12):3580-3584, 2001), and aurastatin E and the like. Examples of toxins that are less preferred in the compositions and methods of the invention include, but are not limited to, poisonous lectins, plant toxins such as ricin, abrin, modeccin, botulina and diphtheria toxins. Of course, combinations of the various toxins could also be coupled to one molecule of a binding agent thereby accommodating variable cytotoxicity. Other chemotherapeutic agents are known to those skilled in the art.

The coupling of one or more toxin molecules to a binding agent is envisioned to include at least one of many chemical mechanisms, for instance covalent binding, affinity binding, intercalation, coordinate binding, and complexation. The toxic compounds used to prepare the immunotoxins are attached to the binding agents by standard protocols known in the art.

According to some aspects of the invention, compositions containing the binding agents are provided. The compositions may contain any of the foregoing binding agents, for example binding polypeptides, (as therapeutic agents) in an optional pharmaceutically acceptable carrier. Thus, in related aspects, some embodiments of the invention provide a method for forming a medicament that involves placing a therapeutically effective amount of the therapeutic agent in the pharmaceutically acceptable carrier to form one or more doses. The effectiveness of treatment or prevention methods of the invention can be determined using standard diagnostic methods described herein.

Therapeutic compositions of the present invention are administered in pharmaceutically acceptable preparations. Such preparations may contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Examples of physiologically and pharmaceutically acceptable carriers include, without being limited to, diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

Therapeutics according to some embodiments of the invention can be administered by any conventional route, for example injection or gradual infusion over time. The administration may, for example, be oral, intravenous, intratumoral, intraperitoneal, intramuscular, intracavity, subcutaneous, or transdermal. When antibodies are used therapeutically, an exemplary route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712). Those of skill in the art can readily determine the various parameters and conditions for producing antibody aerosols without undue experimentation.

The compositions of some embodiments of the invention are administered in effective amounts. An "effective amount" is that amount of a composition that alone, or together with further doses, produces the desired response, e.g. a decrease of the level of phosphorylated paratarg or paraprotein/s binding phosphorylated paratarg in a subject, or a reduction or inhibition of the native activity of phosphorylated paratarg or paraprotein/s binding phosphorylated paratarg in a subject. In some cases of treating a particular disease or condition characterized by the presence of phosphorylated paratarg or paraprotein/s binding phosphorylated paratarg, such as a paratarg positive gammopathy, the desired response is inhibiting the progression of the disease. This may involve slowing the progression of the disease temporarily, although more preferably, it involves halting the progression of the disease permanently. In some cases, the desired response to treatment is a permanent return of the levels of phosphorylated paratarg or paraprotein/s binding phosphorylated paratarg to levels comparable to those found in healthy individuals. In some cases, the desired response to treatment can be delaying or preventing the manifestation of clinical symptoms characteristic for the disease or condition.

The effect of treatment can be monitored by routine methods or can be monitored according to diagnostic methods of the invention discussed herein.

The effective amount will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Pharmaceutical compositions according to some embodiments of this invention some of which are exemplified in the foregoing methods preferably are sterile and contain an effective amount of one or more therapeutic agents as described herein for producing the desired response in a unit of weight or volume suitable for administration to a patient. The response can, for example, be measured by determining the level of phosphorylated paratarg or paraprotein/s binding phosphorylated paratarg in a body fluid of a subject after treatment by immunoassay, e.g. an enzyme-linked immunosorbent (ELISA) assay. Other suitable assays will be known to one of ordinary skill in the art and can be employed for measuring the level of the response.

The doses of one or more therapeutic agents as described herein (e.g., polypeptide, peptide, antibody) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Administration of polypeptide compositions to mammals other than humans, e.g. for testing purposes or veterinary therapeutic purposes, is carried out under substantially the same conditions as described above.

The pharmaceutical compositions may contain suitable buffering agents, for example acetic acid in a salt, citric acid in a salt, boric acid in a salt, and/or phosphoric acid in a salt.

The pharmaceutical compositions also may contain, optionally, suitable preservatives, such as: benzalkonium chloride, chlorobutanol, parabens and/or thimerosal.

The pharmaceutical compositions may conveniently be presented in unit dosage form and may be prepared by any of the methods well-known in the art of pharmacy.

All methods may include the step of bringing the active agent into association with a carrier which constitutes one or more accessory ingredients. In general, compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other examples of compositions include suspensions in aqueous liquids or non-aqueous liquids such as a syrup, elixir or an emulsion. Examples of compositions for parenteral administration include, without being limited to, sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, for example saline and buffered media. Examples of parenteral vehicles are sodium chloride solution, Ringer's dextrose, dextrose and sodium chloride, and lactated Ringer's or fixed oils. Examples for intravenous vehicles are fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like.

The pharmaceutical agents of some embodiments of the invention may be administered alone, in combination with each other, and/or in combination with other drug therapies and/or treatments. Examples of therapies and/or treatments may include, but are not limited to: surgical intervention, chemotherapy, radiotherapy, and adjuvant systemic therapies.

In some embodiments, the invention also provides one or more pharmaceutical kits comprising one or more containers comprising one or more of the pharmaceutical compounds or agents of the invention. Additional materials may be included in any or all kits of the invention, and such materials may include, but are not limited to, for example, buffers, water, enzymes, tubes, control molecules, etc. One or more kits may also include instructions for the use of the one or more pharmaceutical compounds or agents of the invention for the treatment of a gammopathy.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean " either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

EXAMPLES

Experimental Procedures

Patient Data

The study was approved by the local ethical review board ("Ethikkommission der Ärztekammer des Saarlandes") and conducted according to the Declaration of Helsinki. Recombinant DNA work was performed with permission and according to the regulations of local authorities (Government of Saarland). Human materials were obtained during routine diagnostic or therapeutic procedures after obtaining written informed consent and stored at −80° C.

Patients who were diagnosed to have a paraprotein during routine diagnosis (immunofixation and electrophoresis) were randomly chosen for participation in this investigation (n=474), irrespective of their clinical diagnosis. The group of paraprotein positive patients, 279 male and 195 female patients, had a mean age of 64.7 years. The paraprotein distribution was: 65 IgA, 314 IgG, 60 IgM, 22 oligoclonal, 13 BJ). The control group consisted of healthy blood donors (n=30).

Diagnostic Analysis

Immunofixation was done using precast agarose gels in a Hydrasis instrument (SEBIA) according to the manufacturer's instructions. Serum protein electrophoresis was done on a Paragon CZE™ 2000 capillary zone electrophoresis system (Beckman-Coulter).

Screening Analysis

Screening analyses were performed on hEx1 high-density protein expression cDNA libraries, created in Hans Lehrach's laboratory at the Max Planck Institute for Molecular Genetics in Berlin (Germany) and obtained from the Reference Center of the German Human Genome Project (RZPD) (Bussow et al, 1998). These high-density filter membranes display proteins that were expressed from a modified pQE protein expression vector (Qiagen). This vector featured a hexahistidine tag, a T5 promoter and two lac operator sequences, which allowed repression during the growth phase by overexpression of the Lac repressor protein, and subsequent induction of protein expression with isopropyl-beta-D-thiogalactopyranoside (IPTG).

Serum Profiling on High Density Protein Arrays

High density protein arrays of the protein expression set of the hEx1 library were obtained from the German Resource Center for Genome Research (RZPD) and provided by Dr. Mahlknecht from our department. They consist of 37,200 independent clones derived from a human fetal brain cDNA expression library and were used for autoantibody detection. For serum profiling, the filters were blocked in 10% (w/v) non-fat, dry milk powder in TBST (TBS, 0.1% (v/v) Tween 20) at 4° C. overnight, washed twice in TBST, and incubated for 1 h with serum pool #1 at a dilution of $1:10^8$ for each serum. Following three 30-min TBST washes and subsequent incubation with the secondary antibody (goat anti-human IgG biotinylated, Dianova, diluted 1:2.500) and Strep-PDX (1:15.000) in 2% (w/v) Milk/TBST, the filters were washed three times for 30 min in TBST. This was followed by detection using Pharmacia ECL system. Positive signals were localized according to the manufacturer's protocol. Corresponding clones were obtained from RZPD.

Protein Expression

For Western blot analyses, proteins were purified from 500 ml of bacterial cultures grown at 37 ° C. Expression of proteins fused with a $His_6$ tag was induced in the cultures with 1 mM isopropyl -D-thiogalactopyranoside at an $A_{578}$ of 0.6-0.7. After 4 h cells were pelleted, resuspended in 10 ml of buffer B (20 mM Tris/HCl pH 8.0, 0.05% Triton X100, 0.4 µM PMSF, 10 µM Leupeptin, 1 mg/ml Lysozyme) and incubated at 4° C. for 20 min. HiTRAP-chelating columns (Pharmacia) containing 1 ml nickel-nitrilotriacetic acid-agarose (Qiagen) were equilibrated twice with 10 ml of buffer B. After centrifugation, 10 ml of the cell lysate were loaded onto the columns, which were subsequently washed three times with 10 ml of buffer B+10 mM Imidazole. Elution was performed with 5 ml of buffer B+150 mM Imidazole.

Immunoblot Analyses 100 ng of each recombinant protein were separated by SDS-PAGE and transferred to PVDF membrane (Millipore Immobilon) by semidry blotting. The membrane was blocked in TST/milk buffer (10% milk in 10 mM Tris/HCl, pH 7.5, 150 mM NaCl, 0.1% (v/v) Tween 20) overnight, washed and incubated for 1 h with serum in TST (paraprotein patients serum at a dilution of $1:10^8$ and control patients serum at a dilution of $1:10^3$). After three washings in TST, the membranes were incubated for 1 h at RT with goat anti-human IgG AP-coupled antibody (Dianova) diluted 1:5,000 in TST, subsequently washed in TST followed by AP-development.

Serum Profiling on Protein Spot Arrays $His_6$-tagged fusion proteins were spotted on nitrocellulose membranes. After spotting, the protein arrays were blocked, incubated and detected as described above.

Depletion and affinity purification of patients' serum Recombinant $His_6$-tagged Paratarg protein was immobilized on $Ni^{2+}$ agarose following a published procedure (http://www.flemingtonlab.com/Protocols/AbAffinityPurification-Prot.pdf) adopted to His-tag proteins. Patients' serum (100 µl) was diluted 1:2 (v/v) in PBS and depleted by passing 3 times over the Paratarg column. The flow-trough was checked by immunofixation and serum protein electrophoresis.

Identification of the Paratarg Epitope

The epitopes recognized by the patients' paraproteins were identified as described before (Preuss et al, 2006). In brief: matrix-bound synthesized decamer peptides with 5 amino acids overlaps between every $2^{nd}$ consecutive decamer covering the entire paratarg sequence were used to screen patients sera. Paratarg-specific paraproteins binding to the corresponding paratarg epitopes were visualized by ECL technique according to the suppliers' instructions (PIERCE, Rockford, USA). Finally, matrix stripes were photographed for documentation.

Establishing a Paratarg ELISA

Full-length paratarg was recombinantly expressed in HEK293 cells under control of CMV promoter introducing a FLAG tag at the C-terminus of the protein. Total cell extract was prepared and coated indirectly to Nunc maxisorb plates using anti-FLAG mAb (Sigma). Elisa was performed according standard protocols. Partially truncated paratarg fragments were processed accordingly.

Paratarg Deletion Mutants

Paratarg fragments were obtained by PCR amplification using suitable primers and verified by sequencing. These fragments were subcloned into the vector and expressed as described before.

Immmunohistochemistry

Deparaffinized bone marrow sections were treated with TRS for epitope retrieval, incubated with recombinant $His_6$-paratarg, followed by incubation with mouse anti-$His_6$ antibody and visualization by the APAAP technique according to the manufacturer's (Dako-Cytomation, Glostrup, Denmark) recommendations.

DNA Extraction and Mutation Detection

Genomic DNA from patients and control persons was extracted from blood using Qiagen blood DNA extraction kit. Primers used for amplifications were described by Zhang (Zhang et al, 2006). The PCR products amplified with primers were analyzed by electrophoresis on agarose gels for specificity and further sequenced by automated sequencing. Sequencing results were analyzed with CodonCodeAligner (CodonCode Corporation).

Isoelectric Focusing

Washed erythrocytes were treated with lysis buffer (8M urea, 0.1 M $NaH_2PO_4$, 0.01 M TrisHCl, 0.1% NP40), mixed with 2×IEF loading buffer and subjected to isoelectric focusing using precast gels (Invitrogen IEF pH3-10). Analysis was done according manufacturers protocol (1 h 100 V, 1 h 200 V, 30min 500 V). After semi-dry blotting on PVDF membranes (450 mA, 1 h), immunodetection was done using patients serum at a dilution of $1:10^8$ as described before.

Protein Dephosphorylation

Erythrocytes were washed 3×with PBS followed by lysis in LS buffer (10 mM TrisHCl pH8, 30 min 4° C.). After increasing the concentration of TrisHCl to 100 mM, alkaline phosphatase was added (1 U/µl per 500 µl lysate) and incubated at 37° C. overnight. The phosphatase was inactivated by heating at 80° C. for 10 min. Equal volumes of sample and loading buffer were mixed, followed by IEF and immunodetection as described above.

Cleaving by Endopeptidases

Erythrocytes were washed 3×with PBS followed by lysis in LS buffer (10 mM TrisHCl pH8, 30 min 4° C.). After changing to 100 mM TrisHCl/10mM $CaCl_2$, endopeptidase was added. For chymotrypsin, overnight incubation was done at room temperature, while for trypsin 37° C. were used. As a control incubation served PBS without enzymes. Incubation was stopped by the addition of 2 mM PMSF. Analysis was done by a combination of IEF and immunoblotting as described above.

Site-Directed Mutagenesis

Using the QuikChange II Site-Directed Mutagenesis Kit (Stratagene, La Jolla) and a paratarg DNA fragment coding for aa 1-60-FLAG, mutants were constructed in which the serine groups were changed to alanine groups (Ser17Ala, Ser21Ala, Ser17AlaSer21Ala). These mutants were stably transfected into HEK293 cells.

Complementation Assay

Total lysates of HEK cells expressing FLAG-tagged paratarg fragments were prepared and inactivated by heating ("acceptor lysate"). Cells of healthy donors or patients were lysed with 10 mM Tris pH8 and centrifuged after adding native enzyme extracts ("donor lysate"). Both lysates were mixed and incubated for 48 h at 37° C., followed by IEF and immunodetection using anti-FLAG-mAb.

Lymphoblastoid Cell Lines (LCL)

LCLs were established by infection of PBMCs with EBV as described by Neumann et al (Blood 2005; 106:3105-13).

Inhibition Experiments

Stably transfected cell lines were cultured in the presence of inhibitory compounds as indicated. After 5 d cells were removed and analysed by IEF and immunodetection.

Co-IP

Cell lysates were incubated with antibody I at 4° C. overnight. Antigen-antibody complexes were purified by protein G chromatography, followed by gel electrophoresis and blotting. Immunoanalysis was done using antibody II.

BCR

Diagnostic bone marrow smears were scraped with PBS and centrifuged. The resulting cell pellet was used for isolation of genomic DNA. Variable regions of Ig heavy and light chains were amplified as described. PCR products were sequenced and adapted to pCES vector for expression of His-tagged proteins in *E.coli*. Expression was done in TG1 cells using established procedures. After lysing with PBS the Fab2 products were purified by chromatography, concentrated and used.

Analysis of Mitochondrial Import

Cells were cultured as usual. Mitochondria and cytosol were isolated using a mitochondrial isolation kit (Pierce). Purification was checked by analysing prohibitin distribution.

Example 1

Profiling the Antibody Repertoire of MM or MGUS Patients

In this study we screened a human high-density protein array containing 37,200 independent recombinant proteins derived from a human fetal brain expression library with sera obtained from patients with monoclonal gammopathy of undetermined significance (MGUS) and multiple myeloma (MM).

The signal pattern obtained from the screening with the paraprotein pools at a dilution of $1:10^8$ were compared with the patterns obtained from screening with the control sera from clinically healthy donors and to background incubations. From these data, proteins reacting with highly diluted paraprotein-containing sera were identified. 5'- and 3'-tag sequencing of these clones was performed, and their sequences were used for BLAST searches against public databases at NCBI.

Figure 1:
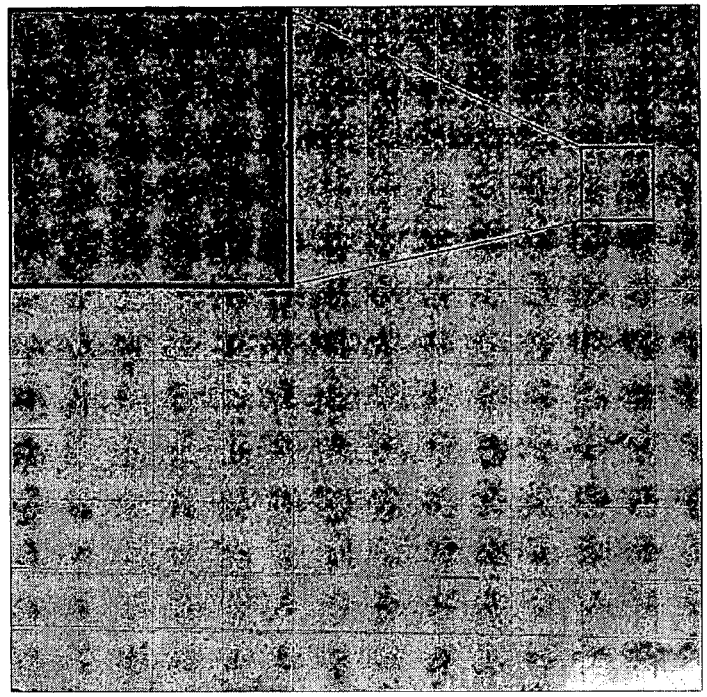
FIG. 1 shows a paraprotein binding pattern (dilution $1:10^8$) in protein macroarray of human fetal brain recombinant proteins. Example of a signal is shown magnified in the inset.

Using serum pool #1 (paraprotein type: 15 IgA, 88 IgG, 11 oligoclonal, n=114) we identified 14 putative paraprotein targets on the human protein filter array (FIG. 1, Tab. 1). Six clones were in reading frame with the $His_6$-tag, three clones were not in reading frame and five clones did not provide clear results. Sequence searches and comparisons using the in-frame sequences identified five known proteins and one unknown gene product derived from chromosome 8. The not-in-frame sequences or the unknown-frame sequences did not allow for the identification of a putative autoantigen even if sequence homology was found.

branes. This corresponded to the state of the proteins immobilized on the PVDF protein array. The nitrocellulose membrane was incubated separately with patients' serum at a dilution of $1:10^8$. This strategy allowed for demonstration of the relevance of the data obtained by screening.

Figure 2:
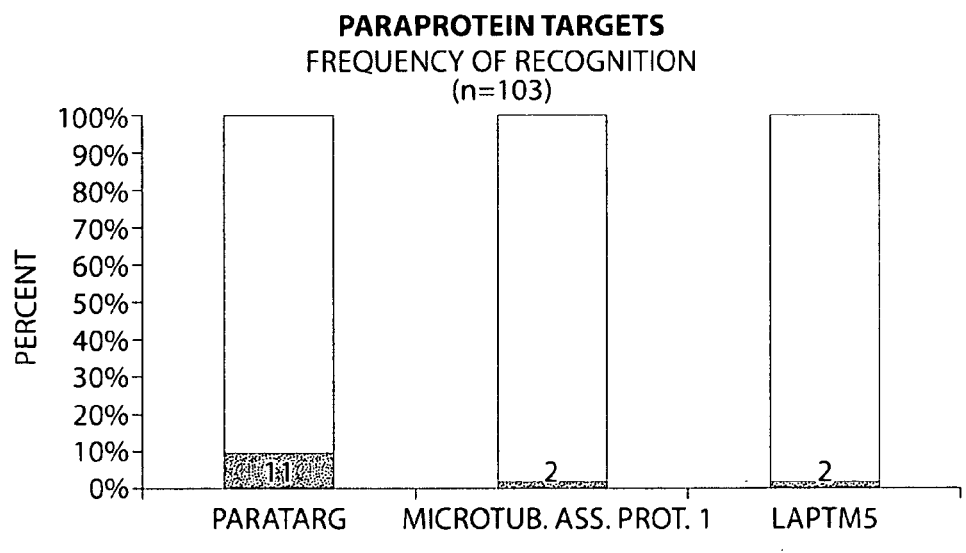
FIG. 2 depicts the recognition frequency of recombinant paratarg, microtub. associated protein 1 and LAPTM5 by paraprotein-containing sera (n=114) at a dilution of $1:10^8$.

In toto, 15 out of 114 paraprotein-containing sera showed an immunoreaction at this high dilution while none of the healthy control sera did so. Most of the signals obtained during the screening procedure were unspecific or reacted with one or two patients' sera (FIG. 2). The signals obtained from clones coding for symplekin, bc12-associated athanogene and alpha-2-HS-Glycoprotein could not be clearly associated with sera of individual patients. One of the strong signals was recognized by 11/114 (9.65%) of the paraprotein-containing sera. The corresponding clone coded for paratarg, previously identified and designated in the data bank as SLP-2 or stomatin-like protein 2.

The results of this screening round indicate that the use of pools of sera instead of single serum incubations is a reliable method for the first screening step on the human filter arrays. We cannot rule out that by using serum pools additional putative autoantigens will/may remain unidentified. However, we expect that the most predominately existing putative autoantigens will be detected by this method.

Figure 4:
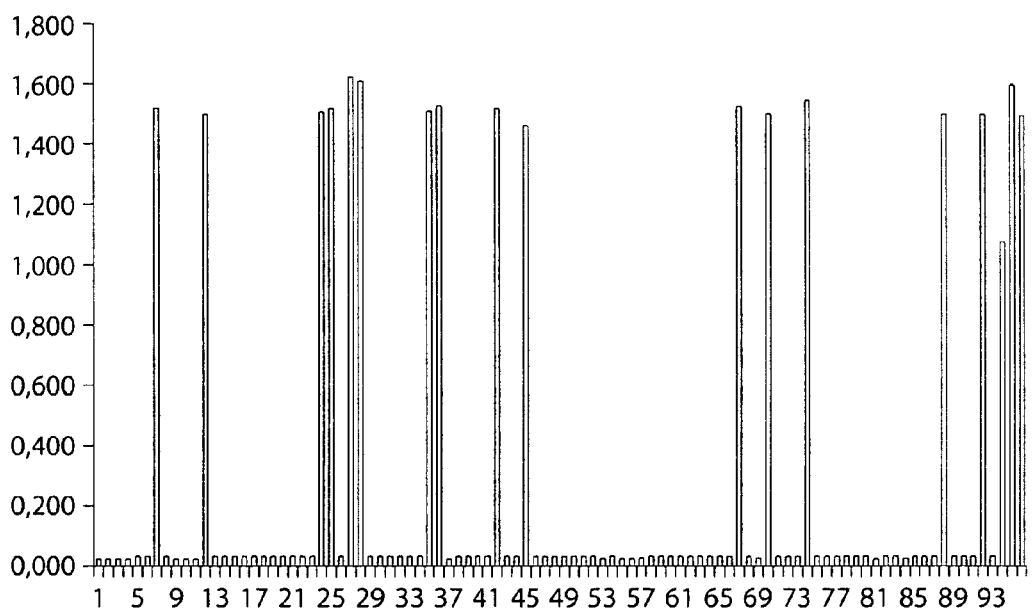
FIG. 4 depicts a paratarg ELISA of paraprotein positive sera. Sera are randomly chosen and tested for paratarg binding at a dilution of $1:10^6$.

To the best of our knowledge, paratarg is the first structure which reacts with a high affinity (titer>$10^8$) with the paraprotein-containing sera of more than two patients: of the first screening round, about 10% of all paraproteins studied recognized paratarg a frequency which is clearly above-random. To exclude the possibility that detection of paratarg using a dot blot assay is a result of the denaturing purification process of recombinant paratarg we expressed paratarg as full-length product in a mammalian system. This product was used for ELISA. There was no difference between results obtained with dot blot or ELISA indicating that recombinant expression, purification and assay technique did not affect the immunoreactivity of paratarg (FIG. 4).

To confirm this high frequency of paratarg recognition by paraproteins at high dilutions, a pool of additional parapro-

TABLE 1

Summary of protein macroarray data from the paraprotein screening

| Signal-quality | RZPD CloneID | ORF | Acc. No. | Name |
|---|---|---|---|---|
| ++ | MPMGp800B08598 | + | NM_022818 | Microtubule-associated proteins 1A/1B light chain 3B precursor |
| ++ | MPMGp800B22602 | + | NM_006762.1 | Lysosomal-associated multitransmembrane protein |
| ++ | MPMGp800E08596 | + |  | Paratarg, SLP-2 |
| + | MPMGp800E08580 | + | NM_004819.1 | Symplekin |
| + | MPMGp800P18577 | ? | NM_004323.3 | (Bcl2-ass. Athanogene) |
| + | MPMGp800P21581 | ? | NM_001622.1 | (alpha-2-HS-Glycoprotein) |
| ± | MPMGp800D11581 | ? |  | Unknown |
| ± | MPMGp800I08601 | − |  | Unknown |
| ± | MPMGp800I15582 | − |  | Unknown |
| ± | MPMGp800J11592 | + | NM_001294.1 | Cleft lip and palate associated transmembrane protein 1 |
| ± | MPMGp800J18600 | ? | NM_182563.2 | Chom. 16 orf 79 |
| ± | MPMGp800K07589 | + | NW_923907.1 | (Chrom 8 part.) |
| ± | MPMGp800L11588 | − |  | unknown |
| ± | MPMGp800M08586 | ? | NW_925940.1 | (Chrom 15 part.) |

Paraprotein-binding quality/strength are ++, + and ±.

Validation of Putative Autoantigens on Protein Spot Arrays

For verification and identification of the reactive patient's serum, six immunopositive clones above (the strongest signals) were expressed in *E.coli* and the corresponding denatured $His_6$-tagged proteins spotted on nitrocellulose memtein-containing sera (serum pool #2, n=260, paraprotein type: 40 IgA, 158 IgG, 47 IgM, 7 oligoclonal, 8 BJ) was analysed by ELISA as described before. This was done in a blinded study. In summary, paratarg was recognized by paraproteins of all Ig types tested with a frequency of 12.9% for IgA, 15.6% IgG and 10.6% for IgM. For details see Table 2.

Figure 3:
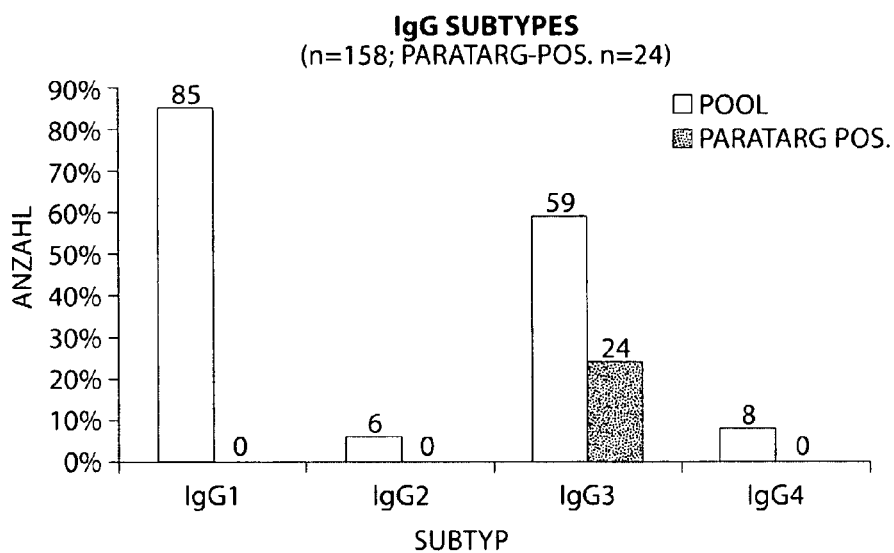
FIG. 3 displays subclasses of paratarg-specific IgG paraproteins. Sera were tested at a dilution of $1:10^8$. The left column of each group represents the IgG sera used for ELISA testing (n=158) while the right column of each group represents the Paratarg pos. paraproteins (n=24).

No significant difference was observed between the sera used for the initial screening and the second screening with additional paraprotein-containing sera with respect to Ig distribution, kappa/lambda distribution, age and sex. Surprisingly, we found that all paratarg-specific IgG paraproteins were of the IgG$_3$ subtype, and 41% of all IgG$_3$ paraproteins had anti-paratarg activity. (FIG. 3).

TABLE 2

Summary of paraproteins tested for anti-paratarg reactivity by ELISA sera used (1:10$^8$)

| Immuno-fixation | all | All | all (%) | positive | positive (%) | positive | positive in group (%) |
|---|---|---|---|---|---|---|---|
| IgA-kappa | 22 | | 9.24 | 4 | 1.68 | | |
| IgA-lambda | 17 | | 7.14 | 1 | 0.42 | | |
| IgA | | 39 | | | | 5.00 | 12.82 |
| IgG-kappa | 96 | | 40.34 | 14 | 5.88 | | |
| IgG-lambda | 57 | | 23.95 | 10 | 4.20 | | |
| IgG | | 153 | | | | 24.00 | 15.69 |
| IgM-kappa | 25 | | 10.50 | 3 | 1.26 | | |
| IgM-lambda | 21 | | 8.82 | 2 | 0.84 | | |
| IgM | | 46 | | | | 5.00 | 10.87 |
| N | 238 | | | 34 | 14.29 | | |

Demonstration of Specificity

Figure 5:
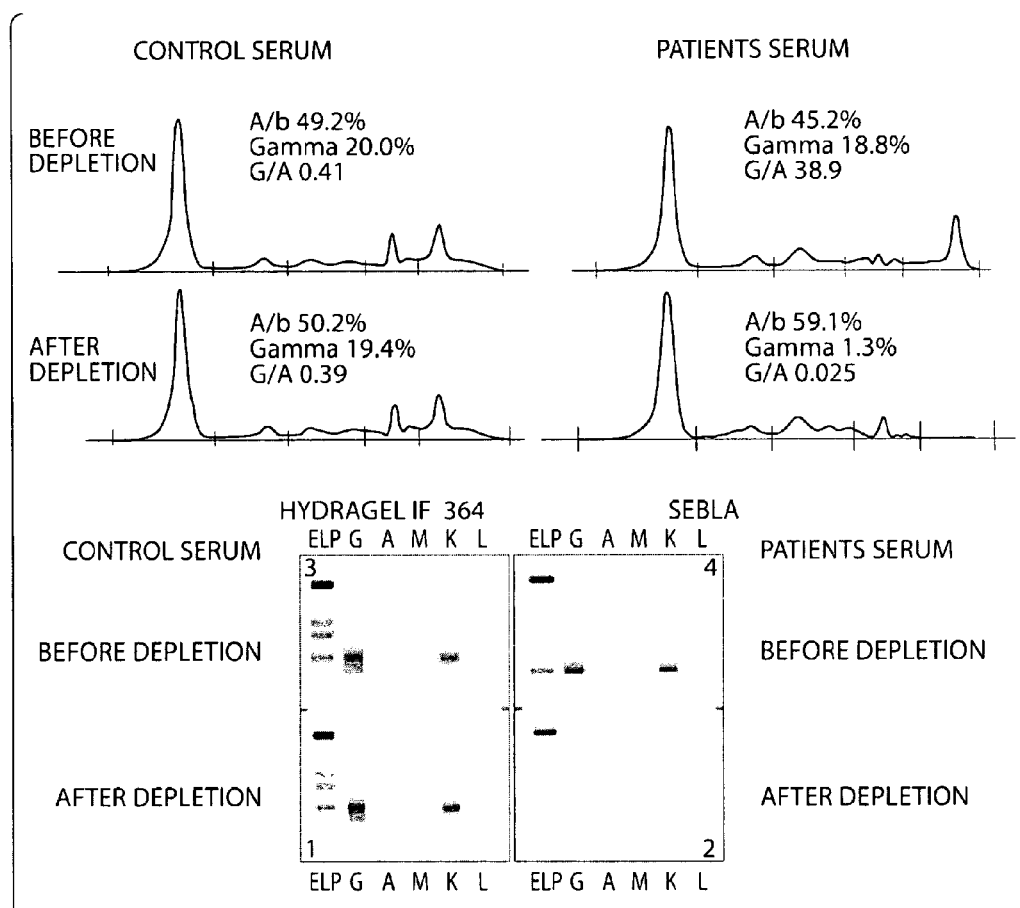
FIG. 5 describes the absorption of anti-paratarg paraprotein from the serum of a patient. Right side from top to bottom: serum electrophoresis of patient serum before depletion including quantification; same serum after depletion of the paraprotein by Paratarg affinity chromatography; immunofixation analysis of the serum before and after depletion. Left side: same as right side using a Paratarg negative paraprotein serum (control).

Two of the paratarg-specific paraproteins were investigated in more detail. Binding specificity of the respective paraproteins to paratarg was further evaluated by absorption studies. Affinity chromatography of patients serum using matrix-immobilized recombinant paratarg showed selective binding of the M-protein to the immobilized paratarg. Other serum components were not retained on the columns nor were proteins and M-protein from another patient whose paraprotein was not paratarg specific (FIG. 5).

Figure 6:
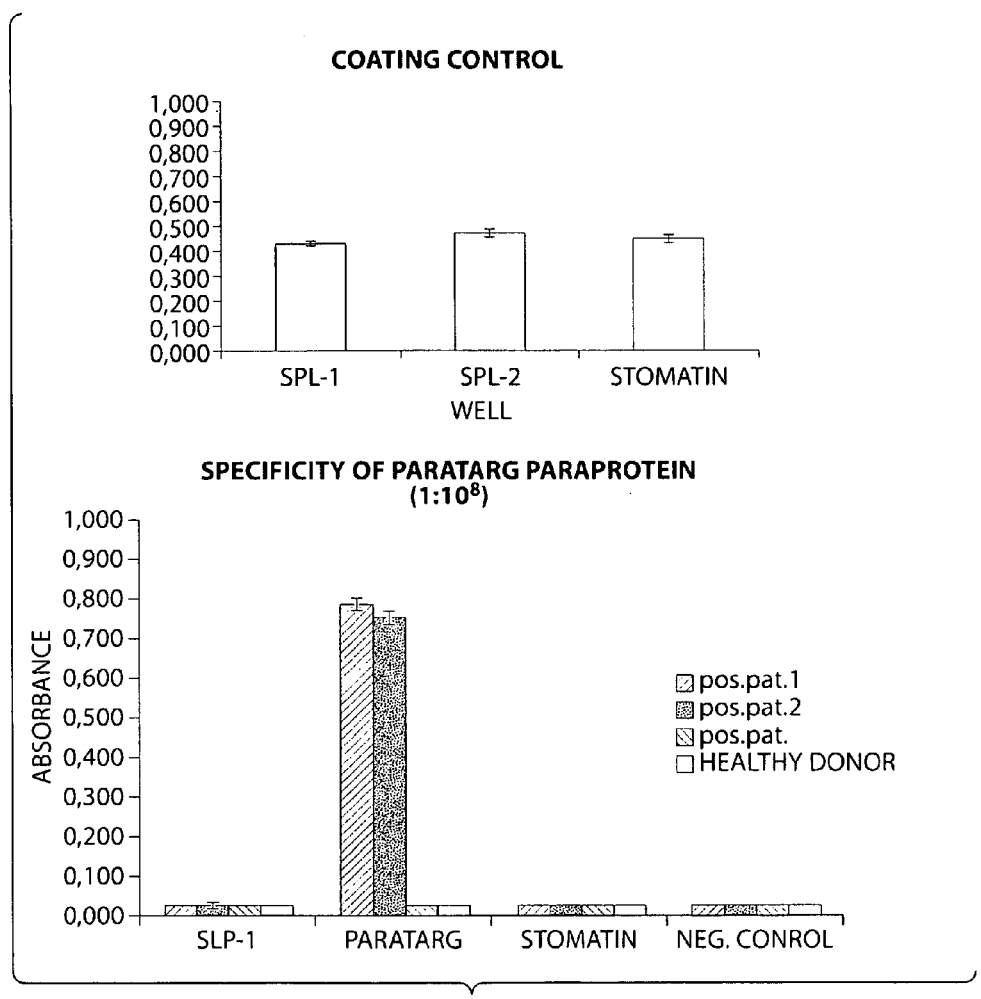
FIG. 6 illustrates the specificity of the paratarg paraprotein. ELISA data of Paratarg paraprotein binding from different patients and control persons at a dilution of $1:10^8$ versus recombinant SLP-1, Paratarg and human stomatin. Sera used were from two Paratarg positive patients (represented by the two left columns in each group), one Paratarg negative patient (second column from right in each group) and a healthy donor (right column in each group). Neg. control means binding of the sera to a non-coated well. The inset shows the equal coating of the α-FLAG-mAb.

These data clearly show that paratarg is the antigen which is recognized by the paraprotein in the respective patients' serum. Paratarg (SLP-2, stomatin-like protein 2) is an unusual member of the stomatin family (Wang & Morrow, 2000; Owczarek et al, 2001). Its derived amino acid sequence predicts a 38.5 kDa protein that is overall ~20%, similar to human stomatin. Paratarg contains a domain with significant similarity to a 172 amino acid region of the HSA stomatin polypeptide which is also present in other members of the stomatin family like SLP-1. Specificity of the paraprotein binding could be shown by recombinantly expressing the human family members SLP-1, paratarg and stomatin followed by Western blotting and ELISA. Paraprotein binding was absolutely specific for to paratarg (FIG. 6), with no cross-reactivity to the other family members.

Example 2

Identification of the Paraprotein-Binding Epitope of Paratarg

Figure 7A:
FIG. 7a identifies the epitope recognized by Paratarg paraprotein at a dilution of $1:10^{10}$ by peptide spot analysis. In this analysis the full-length SLP2 is represented by decamer peptides with an overlap of 5 amino acids. Each spot represents one decamer peptide. The boxed region represents 4 overlapping decamer peptides covering the 17-31 region.
Figure 7B:
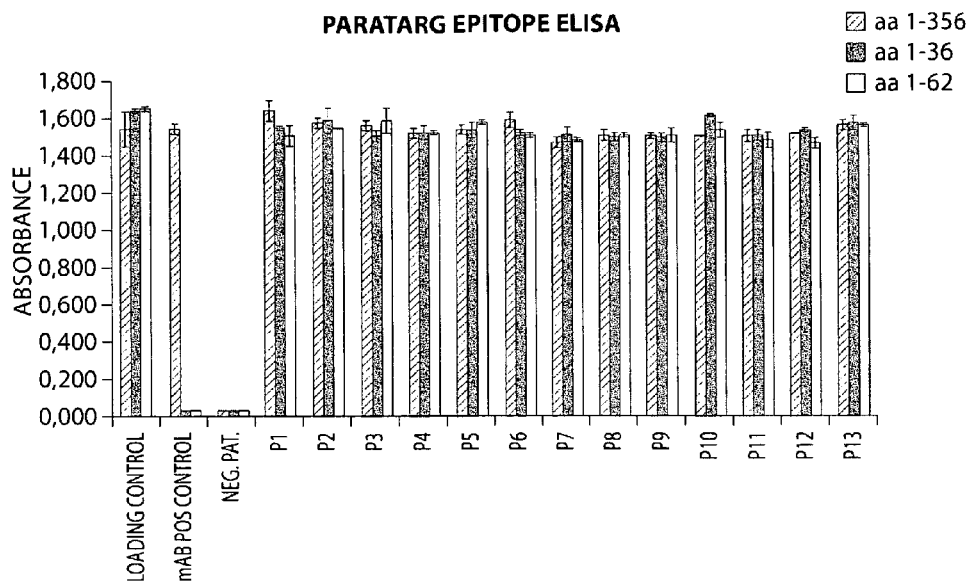
FIG. 7b identifies the epitope recognized by Paratarg paraprotein at a dilution of 1:10$^{10}$ by ELISA. The paraproteins from patients P1 to P13 recognize the same epitope of paratarg (aa 1-36). P0 ("neg. patient") is a patient with a non-paratarg binding paraprotein. All other paraproteins with a paratarg specificity bound to the same epitope. The left bar in each group represents reactivity with aa 1-136 of paratarg, the middle bar in each group represents reactivity with aa 1-36 of paratarg, and the right bar in each group represents reactivity with aa 1-62 of paratarg.

To answer the question if there is a common epitope in the paratarg protein which is recognized by the paraproteins of different patients, peptide spot analysis was done as described. After incubation with patient's serum at a dilution of 1:10$^{10}$, signals were detected representing an epitope near the N-terminal end of Paratarg (FIG. 7a and FIG. 7b).

Figure 8:
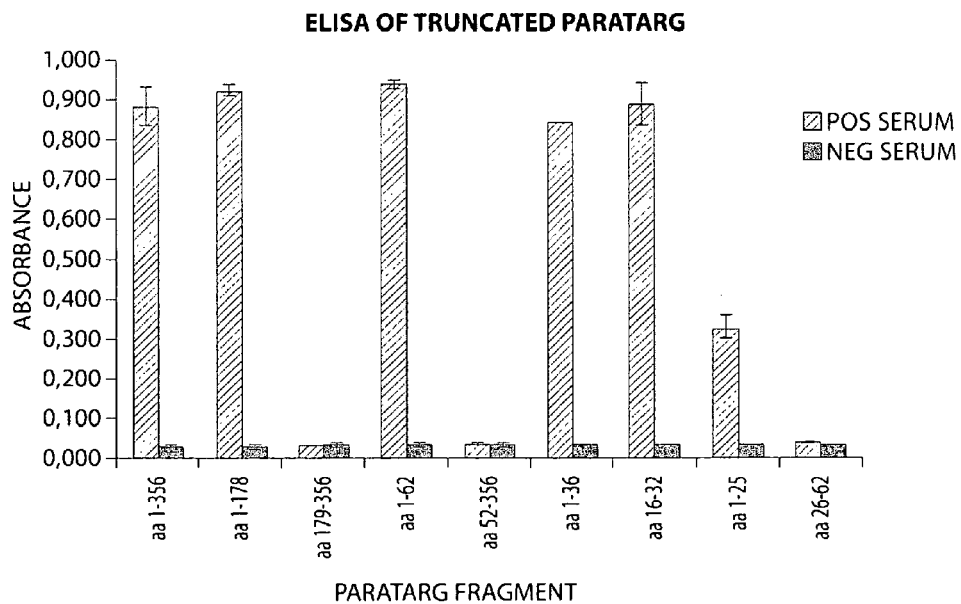
FIG. 8 characterizes recombinantly expressed truncated paratarg fragments recognized by paratarg paraprotein detected by ELISA at a dilution of 1:10$^8$ (example). ELISAs with recombinant fragments of paratarg show that the epitope recognized by paratarg-reactive paraproteins is located between aa 16-25 of paratarg. All paratarg-reactive paraproteins tested recognized this epitope. The left bar in each group represents the use of positive serum, the right bar in each group represents the use of negative serum.

The 15 amino acid region SLLASGRAPRRASSG (SEQ ID NO: 3) shares no homology with other family members. The same result was found when we tested recombinantly truncated paratarg fragments and/or the expressed N-terminal end with patient sera in ELISA (FIG. 8). These results are in agreement with the specificity analysis above because this region shows no homology with other members of the stomatin family.

The paratarg amino acid region SLLASGRAP (SEQ ID NO: 4) was also found to be recognized by anti-paratarg proteins.

Example 3

Characterization of Human Paratarg

Paratarg is a protein with an unknown function that is expressed in all human tissues and hematopoietic cells including erythrocytes (data not shown). To check whether the patient-derived paratarg which reacted with the respective paraprotein was different from paratarg protein in healthy controls or from patients with paraproteins displaying reactivities other than anti-paratarg, paratarg from different patients and healthy controls was sequenced.

The coding sequence of paratarg from all individuals analyzed (n=6) was identical, excluding the possibility that mutations or polymorphisms are responsible for the observed autoimmunogenicity of paratarg in the respective patients. In addition, erythrocyte lysates from patients and controls were subjected to Western blot analysis using a paraprotein with anti-Paratarg activity. All lysates from patients with paraproteins with anti-Paratarg or non-Paratarg specificity and healthy controls showed identical bands in the Western blot (FIG. 9).

IEF Analysis

Detecting no difference in DNA sequences and Western blot analysis we decided to perform isoelectric focusing. Lysed erythrocytes from donors were subjected to this separation technique followed by immunodetection of paratarg using patients' sera or commercially available antibody (e.g. catalogue number 612471 from Becton Dickinson). Comparing lysates obtained from paratarg positive paraprotein patients (14) with paratarg negative paraprotein patients (3) or healthy donors (120) we detected a significant change in mobility.

Only in lysates obtained from erythrocytes of paratarg positive patients did the immunoreactive band shift towards acidic pH indicating a secondary (posttranslational) modification of the paratarg protein. Increasing the numbers of samples subjected to IEF analysis all samples derived from paratarg-immunoreactive patients (n=14) were shown to have a high-titer antibody against paratarg (1:10$^8$), as shown by a shift in IEF analysis indicating a secondary modification of paratarg (FIG. 9, upper part).

Detection of Paratarg Phosphorylation

Figure 11:
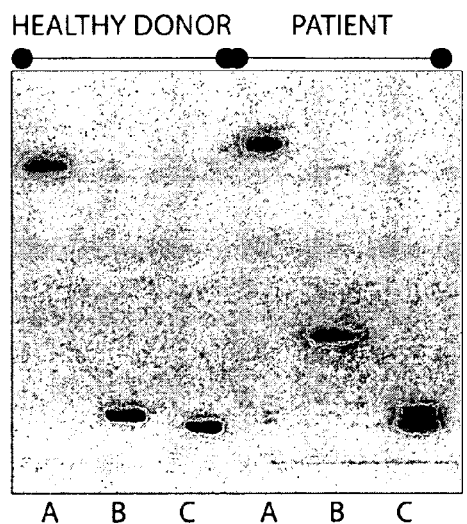
FIG. 11 displays endopeptidase treatment of paratarg derived from patients and healthy controls. Shown is an IEF separation followed by immunodetection with anti-Paratarg as described in methods. A: erythrocyte lysate; B: erythrocyte lysate incubated with chymotrypsin; C: erythrocyte lysate incubated with trypsin.

If the shift of the immunopositive paratarg band in IEF analysis is due to phosphorylation it should be possible to remove the additional phosphorylation by treatment with phosphatase. This could be shown for both groups (FIG. 10). By digestion of paratarg with endopeptidases (trypsin and chymotrypsin, respectively) and comparing patients and controls we were able to show that the additional phosphorylation is located in the region which is recognized by patients' sera, as indicated by an additional immunoreactive band in the tryptic digest of paratarg derived from erythrocytes and separated by IEF (FIG. 11).

Example 4

Family Analysis

Two explanations are possible for the observed association between MM/MGUS patients with anti-paratarg-reactive paraprotein and their modified paratarg protein: paratarg hyperphosphorylation might be inherited or due to an environmental factor. To elucidate this question, blood samples from family members of the patients were analyzed using the methods described above.

Figure 12:
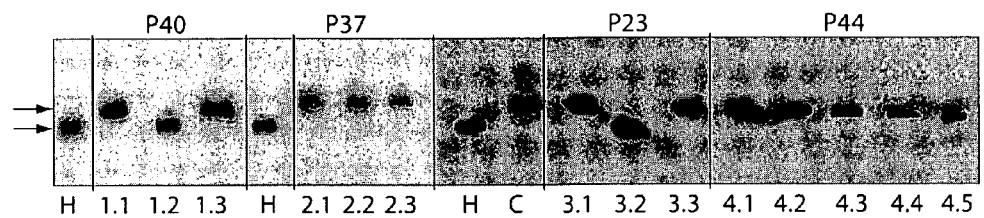
FIG. 12 characterizes paratarg in family members. Shown is an IEF separation followed by immunodetection with anti-Paratarg as described in methods. H: healthy control; C: hyperphosphorylated control; 1.1 female patient P40; 1.2 her husband; 1.3 her son; 2.1 female patient P37; 2.2 her daughter; 2.3 her grandchild; 3.1 male patient P23; 3.2 his wife; 3.3 his daughter; 4.1 female patient P44; 4.2 her daughter; 4.3 her son; 4.4 her sister; 4.5 her brother.

Analyzing six families in respect to this question we detected in all genetic relatives of the patients (children, grandchildren, brothers, sisters) only hyperphosphorylated paratarg while in non-genetic relatives (husbands, wives, adopted children) only unmodified paratarg was present (FIG. 12). In none of the persons analyzed both paratarg modification were found simultaneously. None of the family members included in this study except one person had serological signs of MM/MGUS when analyzed by immunofixation or electrophoresis; in addition, no anti-paratarg antibody at a titer>1:1000 was detected.

However, one family member that had a significant anti-paratarg reactivity was identified as the sister of a female patient, both of whom had an MGUS with a paratarg-specific paraprotein. In summary, our data indicate that the modified paratarg is inherited in a dominant fashion. The fact that all children of index patients studied so far had the modified paraprotein might be explained by the possibility that the index patients are homozygous for the hyperphosphorylated paratarg passing one trait to all their children. Alternatively, the expression of the modified paratarg in all children might be due to a transmissible agent in the germ line.

Example 5

Paratarg in Other Gammopathies and Disorders

We found paraproteins against hyperphosphorylated paratarg also in 5/47 patients with a monoclonal IgM paraprotein which was associated with Morbus Waldenström (or immunocytic lymphoma), as well as one patient with follicular lymphoma with a paraprotein directed against paraprotein and a patient with an immunoblastoma (a variant of diffuse large B-cell lymphoma) and an anti-paratarg specific protein.

Hematopoietic diseases other than multiple myeloma and Morbus Waldenström are not consistently associated with a paraprotein and the frequency of a paraprotein with anti-paratarg activity will have to be determined on a larger patient sample.

In healthy controls, i.e. individuals who tested negative for a paraprotein against phosphorylated paratarg, we found 4/196 to express phosphorylated paratarg, compared to 29/192 patients with MM or MGUS.

Our results indicate that healthy donors expressing the phosphorylated paratarg have an odds ratio of 8.7 (compared to healthy donors not expressing phosphorylated paratarg) to develop an MM/MGUS (p<0.001). The odds ratio for healthy controls expressing phosphorylated paratarg to develop Morbus Waldenström is also increased.

Other malignant diseases (e.g. other lymphomas, chronic lymphocytic leukemia, breast cancer, prostate cancer) are currently investigated in order to answer the question whether carriers of the phosphorylated paratarg are overrepresented in these populations. Should this be the case, it could mean that carriers of the phosphorylated paratarg are also at an increased risk to develop the other respective diseases.

Example 6

Identification of the Phosphorylation Site

As described herein the immunogenic region of paratarg was identified as a 15 aa region (H2N-SLLASGRA-PRRASSG-COOH, SEQ ID NO: 3) near the N-terminal end of the protein. In further ELISA experiments this was narrowed down to aa 16-25. In addition, it was shown by isoelectric focussing that a chymotryptic fragment of paratarg (aa 1-40) derived from patients was hyperphosphorylated when compared to the corresponding fragment of healthy donors. This was also shown for recombinant fragments of aa 1-60 and aa 1-25, while aa 26-60 was not hyperphosphorylated (FIG. 14). Taken together these findings demonstrate that aa 1-25 cover the epitope and the phosphorylation site which is responsible for hyperphosphorylation. Using site-directed mutagenesis on Ser17 and Ser21 (Ser->Ala) followed by expression of these recombinant fragments and complementation assays using enzyme extracts derived from patients and healthy controls, Ser17 was identified as the position where the differential hyperphosphorylation occurs (FIG. 15). In addition, a second phosphorylation was described by Rush et al (Nature Biotechnology 23, 94-101 (2004)), which occurs on Tyr124. This phosphorylation occurs both in patients and healthy controls and is not responsible for hyperphosphorylation of paratarg in patients.

Example 7

Figure 16D:
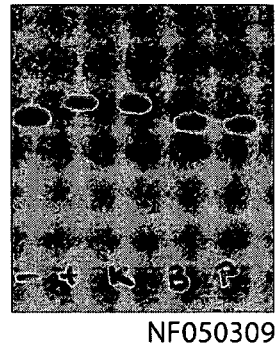

Identification of the Kinase Responsible for Hyperphosphorylation of Paratarg in Patients In MGUS/MM patients and their relatives hyperphosphorylated paratarg is expressed constitutively, while hyperphosphorylation of paratarg is temporary in all healthy persons and cell lines analysed. This was seen by culturing LCLs and cell lines in the presence of kinase or phosphatase inhibitors. The identification of Ser17 as the differential phosphorylation site led to the prediction of a phosphokinase C (PKC) responsible for hyperphosphorylation. Culturing of LCLs and cell lines in the presence of suitable inhibitors (staurosporine, Wortmannin, Bisindolylmaleimid I) at concentrations as indicated below and followed by IEF analysis identifies the PKCzeta isoform as the active kinase (summarized in FIG. 16). This was verified by using highly specific PKC-zeta pseudosubstrate as inhibitor (FIG. 16d). In addition, direct interaction of paratarg and PKCzeta was demonstrated by co-immunoprecipitation experiments in cell lines, LCLs and in total blood (FIG. 17). Finally, the direct interaction between PKCzeta and 17Ser of paratarg was demonstrated by a combination of mutagenesis and co-immunoprecipitation. (FIG. 18).

Example 8

Cloning of the B-Cell Receptor (BCR)

To demonstrate that the high-titered paratarg-antibody present in patients serum is derived from malignant B-cells/plasma cells, the B-cell receptor was cloned from archived diagnostic bone marrow smears followed by recombinant expression. The recombinant BCR showed identical characteristics in ELISA and Western blotting experiments when compared to complete human serum containing natural paratarg-specific paraprotein as summarized in FIG. 19, which shows representative results from of 1 of 2 patients.

Example 9

Mitochondrial Import of Paratarg

Figure 20C:
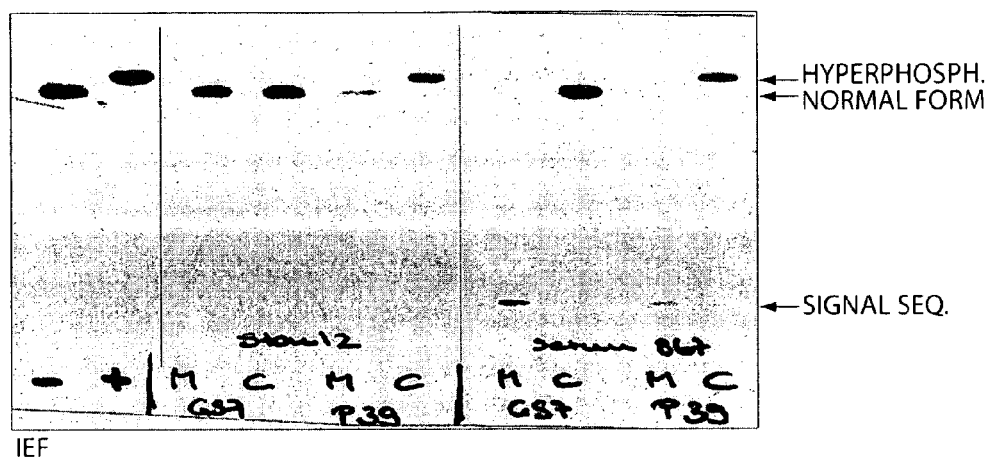

Computer analysis of paratarg predicts a signal sequence for mitochondrial import. The predicted localisation of paratarg is in agreement with published experimental data derived from healthy controls. We therefore analysed the subcellular distribution of paratarg in patients. As seen in FIG. 20 paratarg protein is imported into the mitochondria and the signal sequence is removed during this process. In agreement with our previous data only the signal sequence reacted with the paraprotein from patients' sera. The distribution of paratarg in mitochondria and cytosol was different: in healthy donors ca. 70% of paratarg is imported into the mitochondrium while this figure is only 30% in patients. The role of hyperphosphorylation in this mitochondrial import is not clear; however, we observed that the free signal sequence in the mitochondrium is not phosphorylated any more (FIG. 20c).

Example 10

Paratarg in Lymphoblastoid Cell Lines (LCLs)

We demonstrated that EBV-transformed LCL have a paratarg phosphorylation pattern which is identical to the one of whole blood cell lysates derived from the same donor. This allows for the use of these LCLs as an unrestricted cellular source for future experiments.

Example 11

Hyperphosphorylated Paratarg in Other Ethnic Groups

To study the prevalence of paratarg in other ethnic groups, the paraproteins from 54 Japanese patients were analysed for paratarg immunoreactivity by ELISA as described before. Similar results were obtained, but the frequency of paratarg-specific paraproteins appears to be lower than in our previously analyzed European population: only the sera of 2/54 patients bound to paratarg. This must be verified by analyzing larger number of patients. Similarly, due to the lack of whole peripheral blood cell lysates, the demonstration of hyperphosphorylation of paratarg in the respective patients is still outstanding.

Example 12

Paratarg in Healthy Blood Donors

Analysis of more than 200 blood samples derived from anonymous healthy blood donors revealed that hyperphosphorylated paratarg is present in ca. 2% of these persons (4/202). Due to data protection aspects, nothing is known about the medical background of these blood donors. Starting with 2 samples we were able to establish a new LCL cell line (BA). Preliminary complementation assays with LCL from healthy donors, patients and BA showed differences: BA is able to phosphorylate and dephosphorylate paratarg like healthy donors, but there are quantitative differences. Patients with hyperphosphorylated Paratarg were able to phosphorylate, but they were unable to dephosphorylate paratarg. Again, more detailed analyses are necessary to confirm and explain these observations.

Example 13

Inheritance of Hyperphosphorylated Paratarg

Analysis of family members of patients revealed that the hyperphosphorylated version of paratarg is inherited in a dominant fashion. Two percent of healthy donors are carriers of hyperphosphorylated paratarg-7. This results in an odds ratio of 7.9 for carriers of the hyperphosphorylated paratarg to develop MGUS/MM.

Discussion

This is the first description of the identification of a paraprotein-target which reacts with a considerably proportion of human paraproteins. Until now, the literature on paraproteins includes descriptions of paraprotein targets that were identified just by chance during clinical processes. There are case reports of paraprotein binding to p24 gag protein of HIV, cytomegalovirus or streptolysin-O. There are some reports of a systematic approach to identify target antigens using the phage display technique. This led to the definition of some epitopes, but the identification of the target antigen was rather speculative. In the respective reports paraprotein titers were described as "out of normal range" or they were about $10^4$. Another systematic attempt was pursued by us using SEREX (serological identification of antigens by expression cloning) which allows the systematic screening of putative antibody-antigen interactions, even if neither the antigen nor the antibody are known. This led to the identification of high-titered targets like TPP2, IGFBP2 or porcine kinesin which were recognized by paraprotein-containing sera at a titer of $10^9$ to $10^{10}$.

Here we describe the use of a complex human high-density protein macroarry for screening representing E. coli-expressed proteins (~37.000) originally derived from a human fetal brain cDNA library. The membranes were incubated with a highly-diluted serum pool consisting of 114 individual sera, each at $1:10^7$ final dilution. The use of serum pools instead of higher numbers of individual samples reduces the requirements of materials, e.g. the high density protein arrays, as well as of time and labor. The data sets obtained from screenings of the serum pools were compared with data sets obtained from screening with a pool of 10 control sera from clinically healthy persons and to background incubations with anti-human IgG. From these data, proteins reacting with antibodies present in paraprotein patient serum pools were identified. When we considered proteins that were detected by antibodies from the patient pools, but not by antibodies from the control sera, we identified a subset of 14 proteins. Sequencing of these clones was performed, and their sequences were used for BLAST searches against the public databases including GenBank™ and Unigene.

Individual correlations were done when the identified proteins were expressed as $His_6$-tagged proteins and tested for immunoreactivity using individual sera, each at a $10^8$ dilution. By this approach we identified three proteins with a highly specific immunoreactivity with more than one patient serum, namely paratarg, LAPTM5 and microtubule-associated proteins 1A/1B light chain 3B precursor. The latter two targets were recognized by the serum of two patients, while paratarg was recognized by the sera of 11 out of 114 patients (9.65%). Paratarg recognition was detectable at dilutions of $10^{10}$.

To confirm our original findings with paratarg we analysed 192 additional patients in a blinded study; of these, the paraproteins of 34 patients showed immunoreactivity resulting in an overall frequency of 15.1%. In additions, the specificity of the paratarg reactivity was demonstrated, with no signal obtained using similarly prepared SLP-1 or stomatin which are also members of the stomatin protein family. Remarkably, all IgG paraproteins with anti-paratarg reactivity belonged to the $IgG_3$ subclass (24/158), resulting in an anti-paratarg frequency among the $IgG_3$ paraproteins of 41% (24/59).

To further confirm the presence of paraprotein autoantibodies against the putative autoantigen we used the immobilized recombinantly expressed autoantigens for the absorption of the corresponding patients' sera. By this approach the M-protein was eliminated from the serum as shown by immunoelectrophoresis and immunofixation.

In a next step, we examined the parataⅾg protein in more detail to find hints why it is immunogenic in the respective patients, but not in other people. There were no differences in the DNA sequence between patients and controls, excluding mutations or polymorphisms as a reason for the observed autoimmunogenicity. In addition, Western blot analysis showed identical bands for parataⅾg derived from patients and controls. However, by isoelectric focusing a significant difference in mobility between the parataⅾg derived from patients and controls was shown. All samples derived from patients with an anti-parataⅾg paraprotein (14) showed a shift of the parataⅾg band towards acidic pH while all other samples did not (120 healthy people, 3 parataⅾg-immunonegative MM/MGUS patients). This indicates an additional phosphorylation of the parataⅾg protein in the respective patients. This finding was verified by treatment of the protein samples with phosphatases resulting in protein bands with similar behavior on IEF gels.

We also identified the epitope which is recognized by the patients' sera. Using peptide spot analysis and ELISA on truncated parataⅾg expression products, a 15 amino acid region near the N-terminal end of parataⅾg SLLASGRAPRRASSG (SEQ ID NO: 3) was recognized by patients' serum. Endopeptidase treatment and analytics showed that the immunogenic region is hyperphosphorylated resulting in a difference in mobility during IEF analysis.

Why parataⅾg is hyperphosphorylated in this group of patients, remains to be clarified. Analysis of family members of our patients should give an answer. Surprisingly, we found that all genetic relatives (brothers, sisters, children, grandchildren) of our patients carried the hyperphosphorylated parataⅾg, while non-genetic relatives (husbands, wives, adopted children) did not (6 families, in total 12 persons). None of the family members except one person had a parataⅾg titer or symptoms of MM/MGUS in routine diagnosis. There was one person showing parataⅾg hyperphosphorylation, a high anti-parataⅾg titer, an M-gradient in serum electrophoresis and a paraprotein in immunofixation; and she was identified of the sister of a female patient who had also an MGUS with an anti-parataⅾg specificity, indicating the hyperphosphorylated parataⅾg might be a marker for patients at risk for developing familial MM/MGUS. The reason why consanguineous relatives of index patients have hyperphosphorylated parataⅾg, but no signs of MGUS/MM remains unclear. Only a long-term follow up will allow determining whether these persons will develop MGUS/MM with a longer exposition to the hyperphosphorylated parataⅾg.

REFERENCES

Bussow, K., Cahill, D., Nietfeld, W., Bancroft, D., Scherzinger, E., Lehrach, H., & Walter, G. (1998) A method for global protein expression and antibody screening on high-density filters of an arrayed cDNA library. *Nucleic Acids Res.*, 26, 5007-5008.

Bussow, K., Nordhoff, E., Lubbert, C., Lehrach, H., & Walter, G. (2000) A human cDNA library for high-throughput protein expression screening. *Genomics*, 65, 1-8.

Cahill, D. J. & Nordhoff, E. (2003) Protein arrays and their role in proteomics. *Adv.Biochem.Eng Biotechnol.*, 83, 177-187.

Colwell, N. S., Tollefsen, D. M., & Blinder, M. A. (1997) Identification of a monoclonal thrombin inhibitor associated with multiple myeloma and a severe bleeding disorder. *Br.J.Haematol.*, 97, 219-226.

Jeppsson J O, Laurell C B, & Franzen B (1979) Agarose gel electrophoresis. *Clin Chem*, 25, 629-638.

Konrad, R. J., Kricka, L. J., Goodman, D. B., Goldman, J., & Silberstein, L. E. (1993) Brief report: myeloma-associated paraprotein directed against the HIV-1 p24 antigen in an HIV-1-seropositive patient. *N.Engl.J.Med.*, 328, 1817-1819.

Katzel, J. A., Hari, P., Vesole, D. H. (2007) Multiple myeloma: charging toward a bright future. CA Cancer J Clin. 57, 301-318

Kyle, R. A. (1994) The monoclonal gammopathies. *Clin.Chem.*, 40, 2154-2161.

Landgren, O., Gridley, G., Turesson, I., Caporaso, N. E., Goldin, L. R., Baris, D., Fears, T. R., Hoover, R. N., Linet, M. S. (2006) Risk of monoclonal gammopathy of undetermined significance (MGUS) and subsequent multiple myeloma among African American and white veterans in the United States. Blood 107, 904-906

Lueking, A., Possling, A., Huber, O., Beveridge, A., Horn, M., Eickhoff, H., Schuchardt, J., Lehrach, H., & Cahill, D. J. (2003) A nonredundant human protein chip for antibody screening and serum profiling. *Mol.Cell Proteomics.*, 2, 1342-1349.

Owczarek, C. M., Treutlein, H. R., Portbury, K. J., Gulluyan, L. M., Kola, I., & Hertzog, P. J. (2001) A novel member of the STOMATIN/EPB72/mec-2 family, stomatin-like 2 (STOML2), is ubiquitously expressed and localizes to HSA chromosome 9p13.1. *Cytogenet.Cell Genet.*, 92, 196-203.

Preuss, K. D., Held, G., Kubuschok, B., Hung, C. Z., Malatsidze, N., Wagner, M., & Pfreundschuh, M. (2007) Identification of antigenic targets of paraproteins by expression cloning does not support a causal role of chronic antigenic stimulation in the pathogenesis of multiple myeloma and MGUS. *Int.J.Cancer*, 121, 459-461.

Preuss, K. D., Regitz, E., Neumann, F., & Pfreundschuh, M. (2006) B-cell epitopes from the cancer testis antigen NY-ESO-1. *Int.J.Cancer*, 118, 253.

Seligmann, M. & Brouet, J. C. (1990) Antibody activity of human monoclonal immunoglobulins. *Pathol.Biol. (Paris)*, 38, 822-823.

Sompuram, S. R., Bastas, G., Vani, K., & Bogen, S. A. (2008) Accurate identification of paraprotein antigen targets by epitope reconstruction. *Blood*, 111, 302-308.

Szecsi, P. B., Riise, E., Roslund, L. B., Engberg, J., Turesson, I., Buhl, L., & Schafer-Nielsen, C. (1999) Identification of patient-specific peptides for detection of M-proteins and myeloma cells. *Br.J.Haematol.*, 107, 357-364.

Walter, G., Bussow, K., Cahill, D., Lueking, A., & Lehrach, H. (2000) Protein arrays for gene expression and molecular interaction screening. *Curr.Opin.Microbiol.*, 3, 298-302.

Wang, Y. & Morrow, J. S. (2000) Identification and characterization of human SLP-2, a novel homologue of stomatin (band 7.2b) present in erythrocytes and other tissues. *J.Biol.Chem.*, 275, 8062-8071.

Zhang, L., Ding, F., Cao, W., Liu, Z., Liu, W., Yu, Z., Wu, Y., Li, W., Li, Y., & Liu, Z. (2006) Stomatin-like protein 2 is overexpressed in cancer and involved in regulating cell growth and cell adhesion in human esophageal squamous cell carcinoma. *Clin.Cancer Res.*, 12, 1639-1646.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the purposes specified above.

The invention claimed is:

1. A method comprising
determining a level of a paraprotein that selectively binds to phosphorylated paratarg (stomatin-like protein 2) in a body fluid of a subject, optionally wherein the body fluid is blood, serum, lymph, saliva, urine or cerebrospinal fluid, and
comparing said level of said paraprotein to a reference or control level,
wherein if the level of said paraprotein in said body fluid is higher than the reference or control level, then the subject is indicated as having a gammopathy, and
wherein if the level of said paraprotein in said body fluid is not substantially different from the reference or control level, then the subject is not indicated as having a gammopathy;
optionally wherein the step of determining the level of the paraprotein comprises mixing or contacting said sample with a reagent that selectively binds to said paraprotein, said paraprotein selectively binding said paratarg, and/or contacting said sample with a device for assaying the level of one or more of said specific paraprotein/s.

2. The method of claim 1, wherein the level of said paraprotein that selectively binds said paratarg is determined by an immunoassay, comprising:
contacting said body fluid with an antibody that selectively binds said paraprotein, and
detecting and/or quantifying the binding of said antibody to said paraprotein;
wherein said immunoassay is a western blotting assay, an enzyme-linked immunosorbent assay (ELISA), an enzyme-linked immunospot assay (ELISPOT), a lateral flow test assay, an enzyme immunoassay (EIA), a fluorescent polarization immunoassay (FPIA), a chemiluminescent immunoassay (CLIA), an antibody sandwich capture assay, or an isoelectric focusing assay.

3. The method of claim 1, wherein the level of the paraprotein that selectively binds to said paratarg is determined by an immunoassay, comprising
contacting said body fluid with paratarg, or an epitope thereof, or phosphorylated paratarg, or an epitope thereof, and
detecting and/or quantifying the binding of said paratarg, or epitope thereof, or phosphorylated paratarg, or epitope thereof, to said paraprotein;
optionally wherein the paratarg is human paratarg (SEQ ID NO: 1) (RefSeq: NP_038470); and/or
optionally wherein said immunoassay is a western blotting assay, an enzyme-linked immunosorbent assay (ELISA), an enzyme-linked immunospot assay (ELISPOT), a lateral flow test assay, an enzyme immunoassay (EIA), a fluorescent polarization immunoassay (FPIA), a chemiluminescent immunoassay (CLIA), an antibody sandwich capture assay, or an isoelectric focusing assay.

4. The method of claim 3 wherein the parquetry or epitope thereof used to contact the paraprotein comprises a substitution of one or more amino acid residues amenable to phosphorylation with a different amino acid residue mimicking phosphorylation of said paratarg or epitope thereof;
optionally, wherein the paratarg or epitope thereof used to contact the paraprotein comprises a substitution of one or more serine residues of amino acids 13-31 of human paratarg (SEQ ID NO: 1).

5. The method of claim 4, wherein the paratarg or epitope thereof used to contact the paraprotein comprises a substitution of one or more Ser residues of amino acids 17-31 of human paratarg (SEQ ID NO: 1) with a Glu or Asp or Phe residue.

6. The method of claim 5, wherein the paratarg or epitope thereof used to contact the paraprotein comprises a substitution of 17Ser of human paratarg (SEQ ID NO: 1) with a Glu or Asp or Phe residue.

7. The method of claim 1, wherein the paratarg is phosphorylated paratarg, optionally, wherein the paratarg is phosphorylated on/in one or more of amino acids 17-31 of human paratarg (SEQ ID NO: 1), or wherein the paratarg is phosphorylated on amino acid 17 (Ser) of human paratarg (SEQ ID NO: 1).

8. A method comprising determining a level of phosphorylated paratarg (stomatin-like protein 2) in a body fluid, cell, or tissue of a subject, optionally wherein the body fluid is blood, serum, lymph, saliva, urine or cerebrospinal fluid, and
comparing said level of paratarg to a reference or control level,
wherein if the level of paratarg in the subject is higher than the reference or control level, then the subject is indicated as having a gammopathy, and
wherein if the level of paratarg is not substantially different from the reference or control level, then the subject is not indicated as having a gammopathy;
optionally wherein the step of determining the level of paratarg comprises mixing or contacting said sample with a reagent that selectively binds to paratarg, and/or contacting said sample with a device for assaying the level of paratarg.

9. The method of claim 8, wherein the level of paratarg is determined by an immunoassay, comprising
contacting said body fluid with an antibody that selectively binds paratarg, and
detecting and/or quantifying the binding of said antibody to paratarg;
optionally wherein said immunoassay is a western blotting assay, an enzyme-linked immunosorbent assay (ELISA), an enzyme-linked immunospot assay (ELISPOT), a lateral flow test assay, an enzyme immunoassay (EIA), a fluorescent polarization immunoassay (FPIA), a chemiluminescent immunoassay (CLIA), an antibody sandwich capture assay, or an isoelectric focusing assay.

10. The method of claim 8, wherein the paratarg is phosphorylated paratarg, optionally, wherein the paratarg is phosphorylated on/in one or more of amino acids 17-31 of human paratarg (SEQ ID NO: 1), or wherein the paratarg is phosphorylated on amino acid 17 (Ser) of human paratarg (SEQ ID NO: 1).

11. An isolated antibody or antigen-binding fragment thereof that selectively binds a paraprotein, wherein the paraprotein selectively binds phosphorylated paratarg (stomatin-like protein 2).

12. A composition comprising the isolated antibody or antigen-binding fragment thereof of claim 11, optionally wherein the composition comprises a pharmaceutically acceptable carrier.

13. An isolated antibody or antigen-binding fragment thereof that selectively binds phosphorylated paratarg (stomatin-like protein 2) or a phosphorylated epitope thereof.

14. A composition comprising the isolated antibody or antigen-binding fragment thereof of claim 13, optionally wherein the composition comprises a pharmaceutically acceptable carrier.

15. A kit for detecting paratarg (stomatin-like protein 2), or an epitope thereof, or a paraprotein, or fragment thereof, that selectively binds paratarg, comprising
the antibody, or fragment thereof, of claim 11.

16. A kit for detecting paratarg (stomatin-like protein 2), or an epitope thereof, or a paraprotein, or fragment thereof, that selectively binds paratarg, comprising
the antibody, or fragment thereof, of claim 13.

* * * * *

UNITED STATES PATENT AND TRADEMARK OFFICE
CERTIFICATE OF CORRECTION

PATENT NO.       : 8,679,765 B2
APPLICATION NO.  : 13/145597
DATED            : March 25, 2014
INVENTOR(S)      : Preuss et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 92 days.

Signed and Sealed this
Twenty-ninth Day of September, 2015

Michelle K. Lee
*Director of the United States Patent and Trademark Office*

```
                           SEQUENCE LISTING

<160> NUMBER OF SEQ ID NOS: 13

<210> SEQ ID NO 1
<211> LENGTH: 356
<212> TYPE: PRT
<213> ORGANISM: Homo sapiens

<400> SEQUENCE: 1

Met Leu Ala Arg Ala Ala Arg Gly Thr Gly Ala Leu Leu Leu Arg Gly
1               5                   10                  15

Ser Leu Leu Ala Ser Gly Arg Ala Pro Arg Arg Ala Ser Ser Gly Leu
            20                  25                  30

Pro Arg Asn Thr Val Val Leu Phe Val Pro Gln Gln Glu Ala Trp Val
            35                  40                  45

Val Glu Arg Met Gly Arg Phe His Arg Ile Leu Glu Pro Gly Leu Asn
    50                  55                  60

Ile Leu Ile Pro Val Leu Asp Arg Ile Arg Tyr Val Gln Ser Leu Lys
65                  70                  75                  80

Glu Ile Val Ile Asn Val Pro Glu Gln Ser Ala Val Thr Leu Asp Asn
                85                  90                  95

Val Thr Leu Gln Ile Asp Gly Val Leu Tyr Leu Arg Ile Met Asp Pro
            100                 105                 110

Tyr Lys Ala Ser Tyr Gly Val Glu Asp Pro Glu Tyr Ala Val Thr Gln
            115                 120                 125

Leu Ala Gln Thr Thr Met Arg Ser Glu Leu Gly Lys Leu Ser Leu Asp
    130                 135                 140

Lys Val Phe Arg Glu Arg Glu Ser Leu Asn Ala Ser Ile Val Asp Ala
145                 150                 155                 160

Ile Asn Gln Ala Ala Asp Cys Trp Gly Ile Arg Cys Leu Arg Tyr Glu
                165                 170                 175

Ile Lys Asp Ile His Val Pro Pro Arg Val Lys Glu Ser Met Gln Met
            180                 185                 190

Gln Val Glu Ala Glu Arg Arg Lys Arg Ala Thr Val Leu Glu Ser Glu
            195                 200                 205

Gly Thr Arg Glu Ser Ala Ile Asn Val Ala Glu Gly Lys Lys Gln Ala
    210                 215                 220

Gln Ile Leu Ala Ser Glu Ala Glu Lys Ala Glu Gln Ile Asn Gln Ala
225                 230                 235                 240

Ala Gly Glu Ala Ser Ala Val Leu Ala Lys Ala Lys Ala Lys Ala Glu
                245                 250                 255

Ala Ile Arg Ile Leu Ala Ala Ala Leu Thr Gln His Asn Gly Asp Ala
            260                 265                 270

Ala Ala Ser Leu Thr Val Ala Glu Gln Tyr Val Ser Ala Phe Ser Lys
            275                 280                 285

Leu Ala Lys Asp Ser Asn Thr Ile Leu Leu Pro Ser Asn Pro Gly Asp
    290                 295                 300

Val Thr Ser Met Val Ala Gln Ala Met Gly Val Tyr Gly Ala Leu Thr
305                 310                 315                 320

Lys Ala Pro Val Pro Gly Thr Pro Asp Ser Leu Ser Ser Gly Ser Ser
                325                 330                 335

Arg Asp Val Gln Gly Thr Asp Ala Ser Leu Asp Glu Glu Leu Asp Arg
            340                 345                 350
```

```
Val Lys Met Ser
        355

<210> SEQ ID NO 2
<211> LENGTH: 1303
<212> TYPE: DNA
<213> ORGANISM: Homo sapiens

<400> SEQUENCE: 2
ggcttctggg agcgaccgct ccgctcgtct cgttggttcc ggaggtcgct gcggcggtgg      60
gaaatgctgg cgcgcgcggc gcggggcact ggggcccttt tgctgagggg ctctctactg     120
gcttctggcc gcgctccgcg ccgcgcctcc tctggattgc ccgaaacac cgtggtactg      180 ttcgtgccgc agcaggaggc ctgggtggtg agcgaatgg gccgattcca ccggatcctg      240
gagcctggtt tgaacatcct catccctgtg ttagaccgga tccgatatgt gcagagtctc     300
aaggaaattg tcatcaacgt gcctgagcag tcggctgtga ctctcgacaa tgtaactctg     360
caaatcgatg gagtccttta cctgcgcatc atggacccct acaaggcaag ctacggtgtg    420
gaggaccctg agtatgccgt cacccagcta gctcaaacaa ccatgagatc agagctcggc    480
aaactctctc tggacaaagt cttccgggaa cgggagtccc tgaatgccag cattgtggat    540
gccatcaacc aagctgctga ctgctggggt atccgctgcc tccgttatga gatcaaggat    600
atccatgtgc cacccgggt gaaagagtct atgcagatgc aggtggaggc agagcggcgg    660
aaacgggcca cagttctaga gtctgagggg acccgagagt cggccatcaa tgtggcagaa    720
gggaagaaac aggcccagat cctggcctcc gaagcagaaa aggctgaaca gataaatcag    780
gcagcaggag aggccagtgc agttctggcg aaggccaagg ctaaagctga agctattcga    840
atcctggctg cagctctgac acaacataat ggagatgcag cagcttcact gactgtggcc    900
gagcagtatg tcagcgcgtt ctccaaactg gccaaggact ccaacactat cctactgccc    960
tccaaccctg gcgatgtcac cagcatggtg gctcaggcca tgggtgtata tggagccctc   1020
accaaagccc cagtgccagg gactccagac tcactctcca gtgggagcag cagagatgtc   1080
cagggtacag atgcaagtct tgatgaggaa cttgatcgag tcaagatgag ttagtggagc   1140
tgggcttggc cagggagtct ggggacaagg aagcagattt tcctgattct ggctctagct   1200
tccctgccaa gattttggtt tttattttt tatttgaact ttagtcgtgt aataaactca    1260
ccagtggcaa acctgaaaaa aaaaaaaaaa aaaaaaaaa aaa                      1303

<210> SEQ ID NO 3
<211> LENGTH: 15
<212> TYPE: PRT
<213> ORGANISM: Artificial Sequence
<220> FEATURE:
<223> OTHER INFORMATION: Recombinant polypeptide

<400> SEQUENCE: 3

Ser Leu Leu Ala Ser Gly Arg Ala Pro Arg Arg Ala Ser Ser Gly
1               5                   10                  15

<210> SEQ ID NO 4
<211> LENGTH: 9
<212> TYPE: PRT
<213> ORGANISM: Artificial sequence
<220> FEATURE:
<223> OTHER INFORMATION: Recombinant polypeptide

<400> SEQUENCE: 4

Ser Leu Leu Ala Ser Gly Arg Ala Pro
```

-continued

```
<210> SEQ ID NO 5
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 5
tttaaaatgc tggcgcgcgc ggcg                                          24

<210> SEQ ID NO 6
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 6
tttaaaactc atcttgactc gatc                                          24

<210> SEQ ID NO 7
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 7
tttaaaacca ggctccagga tccggtg                                       27

<210> SEQ ID NO 8
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 8
tttaaacgga gcgcggccag aagc                                          24

<210> SEQ ID NO 9
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 9
tttaaaatgc gccgcgcctc ctctgga                                       27

<210> SEQ ID NO 10
<211> LENGTH: 30
<212> TYPE: PRT
<213> ORGANISM: Artificial sequence
<220> FEATURE:
<223> OTHER INFORMATION: recombinant polypeptide

<400> SEQUENCE: 10

Ala Leu Leu Leu Arg Gly Ser Leu Leu Ala Ser Gly Arg Ala Pro Arg
1               5                   10                  15

Arg Ala Ser Ser Gly Leu Pro Arg Asn Thr Val Val Leu Phe
            20                  25                  30

<210> SEQ ID NO 11
```

```
<211> LENGTH: 30
<212> TYPE: PRT
<213> ORGANISM: Artificial sequence
<220> FEATURE:
<223> OTHER INFORMATION: Recombinant polypeptide

<400> SEQUENCE: 11

Ala Leu Leu Leu Arg Gly Ala Leu Leu Ala Ser Gly Arg Ala Pro Arg
1               5                   10                  15

Arg Ala Ser Ser Gly Leu Pro Arg Asn Thr Val Val Leu Phe
            20                  25                  30

<210> SEQ ID NO 12
<211> LENGTH: 30
<212> TYPE: PRT
<213> ORGANISM: Artificial sequence
<220> FEATURE:
<223> OTHER INFORMATION: Recombinant polypeptide

<400> SEQUENCE: 12

Ala Leu Leu Leu Arg Gly Ser Leu Leu Ala Ala Gly Arg Ala Pro Arg
1               5                   10                  15

Arg Ala Ser Ser Gly Leu Pro Arg Asn Thr Val Val Leu Phe
            20                  25                  30

<210> SEQ ID NO 13
<211> LENGTH: 30
<212> TYPE: PRT
<213> ORGANISM: Artificial sequence
<220> FEATURE:
<223> OTHER INFORMATION: Recombinant polypeptide

<400> SEQUENCE: 13

Ala Leu Leu Leu Arg Gly Ala Leu Leu Ala Ala Gly Arg Ala Pro Arg
1               5                   10                  15

Arg Ala Ser Ser Gly Leu Pro Arg Asn Thr Val Val Leu Phe
            20                  25                  30
```